(12) United States Patent
Barbour et al.

(10) Patent No.: US 8,672,918 B2
(45) Date of Patent: *Mar. 18, 2014

(54) METHODS FOR IDENTIFYING AREAS OF A SUBJECT'S SKIN THAT APPEAR TO LACK VOLUME

(75) Inventors: Jennifer Barbour, Denver, CO (US); Martin D. Fisher, Lake Forest, CA (US)

(73) Assignee: IPSYRNG Capital Development, LLC, Denver, CO (US)

(*) Notice: Subject to any disclaimer, the term of this patent is extended or adjusted under 35 U.S.C. 154(b) by 477 days.

This patent is subject to a terminal disclaimer.

(21) Appl. No.: 12/600,468

(22) PCT Filed: Jun. 8, 2007

(86) PCT No.: PCT/US2007/070811
§ 371 (c)(1),
(2), (4) Date: May 10, 2010

(87) PCT Pub. No.: WO2008/143681
PCT Pub. Date: Nov. 27, 2008

(65) Prior Publication Data
US 2010/0262118 A1 Oct. 14, 2010

Related U.S. Application Data

(60) Provisional application No. 60/938,424, filed on May 16, 2007, provisional application No. 60/938,425, filed on May 16, 2007.

(51) Int. Cl.
*A61M 5/178* (2006.01)
*A61B 5/103* (2006.01)

(52) U.S. Cl.
USPC ................. 604/506; 604/511; 600/587

(58) Field of Classification Search
USPC ................. 604/20, 506, 511; 600/587
See application file for complete search history.

(56) References Cited

U.S. PATENT DOCUMENTS

| | | | |
|---|---|---|---|
| 5,007,940 A | 4/1991 | Berg |
| 5,128,326 A | 7/1992 | Balazs et al. |
| 5,143,724 A | 9/1992 | Leshchiner et al. |
| 5,399,351 A | 3/1995 | Leshchiner et al. |
| 5,633,001 A | 5/1997 | Agerup |
| 5,827,937 A | 10/1998 | Agerup |
| 5,843,078 A | 12/1998 | Sharkey |
| 7,192,984 B2 | 3/2007 | Berg et al. |
| 2004/0225276 A1 | 11/2004 | Burgess |
| 2006/0073178 A1 | 4/2006 | Giampapa |
| 2010/0160849 A1 | 6/2010 | Barbour |

OTHER PUBLICATIONS

International Search Report (Form PCT/ISA/210), International Application No. PCT/US2007/70811, International Filing Date Jun. 8, 2007.
International Preliminary Report on Patentability (Form PCT/IPEA/409), International Application No. PCT/US2007/70811, International Filing Date Jun. 8, 2007.
International Search Report (Form PCT/ISA/210), International Application No. PCT/US2007/70806, International Filing Date Jun. 8, 2007.
International Preliminary Report on Patentability (Form PCT/IPEA/409), International Application No. PCT/US2007/70806, International Filing Date Jun. 8, 2007.
Steven H. Dayan, "Botox The Wonder Drug", www.drdayan.com, 2003, (Booklet)119 pages.
Arnold W. Klein et al., "Hyaluronic Acid Fillers and Botulinum Toxin Type A: Rationale for Their Individual and Combined Use of Injectable Facial Rejuvenation", Plastic and Reconstructive Surgery, 81S-88S, 2007, 8 pages.
Murad Alam et al., "ASDS Guidelines of Care: Injectable Fillers", by the American Society for Dermatologic Surgery, Inc., ISSN: 1076-0512, 2008; 34:S115-S148, 34 pages.
Seth L. Matarasso et al., Consensus Recommendations for Soft-Tissue Augmentation with Nonanimal Stabilized Hyaluronic Acid (Restylane), American Society of Plastic Surgeons, 3S-34S, 2006, 32 pages.
"Tissue Augmentation in Clinical Practice", Second Edition, edited by Arnold W. Klein, pp. 291-314 (2006).
International Search Report and Written Opinion dated Oct. 1, 2008, received in International Application No. PCT/US07/70811.
International Search Report and Written Opinion dated Oct. 1, 2008, received in International Application No. PCT/US07/70806.
"Advances in Facial Contouring a Focus on Fillers: Overview of Fillers", released date May 1, 2004, Vanderbilt University School of Medicine, 23 pages.
"Advances in Facial Contouring a Focus on Fillers: Science of Hyaluronic Acid Fillers", released date May 1, 2004, Vanderbilt University School of Medicine, 37 pages.
"Advances in Facial Contouring a Focus on Fillers: Patient Assessment", released date May 1, 2004, Vanderbilt University School of Medicine, 23 pages.
"Advances in Facial Contouring a Focus on Fillers: Patient Comfort Management", released date May 1, 2004, Vanderbilt University School of Medicine, 22 pages.
"Advances in Facial Contouring a Focus on Fillers: Injection Techniques", released date May 1, 2004, Vanderbilt University School of Medicine, 57 pages.
"Advances in Facial Contouring a Focus on Fillers: The Aging Face", released date May 1, 2004, Vanderbilt University School of Medicine, 34 pages.

(Continued)

*Primary Examiner* — Chih-Min Kam
(74) *Attorney, Agent, or Firm* — Marsh Fischmann & Breyfogle LLP

(57) ABSTRACT

The present embodiments relate to methods and systems for identifying areas of a subject's skin that lack sufficient volume. In some embodiments, this can be used to direct the administration of filler compositions or the application of techniques that increase the volume or firmness of the area. In some embodiments, the methods and systems provide for improved aesthetic benefit as well as suitability for instruction and training. In some embodiments, the methods are especially useful in the administration of dermal fillers to a subject.

8 Claims, 11 Drawing Sheets

(56) References Cited

OTHER PUBLICATIONS

"Advances in the Treatment of Facial Wrinkles: New Injection Techniques with Fillers", Johns Hopkins University School of Medicine, released date Apr. 1, 2006, 53 pages.

Bader et al., "Dermal Fillers". eMedicine Dermatology, initially visited May 16, 2007, last updated Oct. 23, 2008, accessed at http://emedicine.medscape.com/articles/1125066-overview, 21 pages.

"Facial Contouring with Restylane", Restylane Redefining Beauty, Medicis Aesthetics, 2004, 32 pages.

Leslie Fletcher, "Injectable Thread Lift", MedEsthetics, Jan./Feb. 2009, 3 pages.

Gary D. Monheit, "Hylaform: A New Hyaluronic Acid Filler", Facial Plastic Surgery, 2004, 20 (2): 153-155, 3 pages.

Rhoda S. Narins et al., "A Randomized, Double-Blind, Multicenter Comparison of the Efficacy and Tolerability of Restylane Versus Zyplast fo the Correction of Nasolabial Folds" Dermatology Surgery 2003, 29(6): (Abstract Only), 2 pages.

D. Thioly-Bensoussan, "A New Option for Volumetric Restoration: Poly-L-Lactic Acid", JEADV, May 2006, vol. 20, Suppl. 1, pp. 12-16.

Van Eijk et al., "A Novel Method to Inject Hyaluronic Acid: the Fern Pattern Technique", Journal of Drugs in Dermatology, Aug. 2007, 10 pages.

Verpaelle et al., "Restylane SubQ, a Non-Animal Stabilized Hyaluronic Acid Gel for Soft Tissue Augmentation of the Mid- and Lower Face", Aesthetic Surgery Journal, 26 (suppl):S10-S17, Jan./Feb. 2006, 16 pages.

Bosniak et al., "Nonanimal Stabilized Hyaluronic Acid for Lip Augmentation and Facial Rhytid Ablation" Archives of Facial Plastic Surgery, vol. 6, No. 6, Nov.-Dec. 2004, (6:379-383), 9 pages.

Steven H. Dayan, "Restylane Fill Me Up", www.drdayan.com, 2006.

Joseph Niamtu III, "New Lip and Wrinkle Fillers", Oral Maxilloficial Surg Clin N Am (2005), pp. 17-28.

Jean D.A. Carruthers et al., "Facial Sculpting and Tissue Augmentation", University of British Columbia, Dermatol Surg 2005; 31:1604-1612, 9 pages.

METHODS FOR IDENTIFYING AREAS OF A SUBJECT'S SKIN THAT APPEAR TO LACK VOLUME

RELATED APPLICATIONS

This application is an application under 35 USC §371 of International Application PCT/US07/070,811, filed Jun. 8, 2007, which claims priority to U.S. Provisional Application No. 60/938,424, filed May 16, 2007, and U.S. Provisional Application No. 60/938,425, filed, May 16, 2007, each of which is herein incorporated by reference in their respective entireties.

BACKGROUND

1. Field of the Invention

Methods and systems relating to the identification of areas that are under volume in a subject's skin are provided.

2. Description of the Related Art

Methods for delivery or injection of fillers into a subject or subject's face for cosmetic purposes are well-known. Despite the fact that such methods are being used with ever increasing frequency, the art has seen little in the way of developments in regard to certain aspects of these injection methods.

SUMMARY

In some aspects, the present disclosure provides techniques for identifying areas in a subject that are under volume. In some aspects, this can be used for the administration of injectable filler compositions. This can be especially relevant to increase the aesthetic benefit of implanted materials or other types of treatment with similar results.

In some aspects, the method is a dynamic or animated method. In some embodiments, one uses various indicators in a subject's face, to determine where the injectable filler should be applied. In some embodiments, one identifies indicators on the subject's face in a first and then a second, different, facial expression. Areas where the indicators overlap or interact between the two facial expressions are areas that can benefit from the application of an injectable filler. Examples of indicators include those areas that are under volume and lines or wrinkles.

In some aspects, a generally applicable, subject-specific injection technique can be employed. In addition, in some embodiments, there is a need for product-specific training methods and systems. In some embodiments, such methods and systems for training can be configured to provide reproducible results. It is therefore desirable to provide a convenient, accurate, reproducible system for targeted, subject anatomy-specific administration of injectable filler compositions and training thereof.

In some aspects, a method for administering an injectable filler composition is provided. In some embodiments, the method can involve identifying at least a first facial line on a subject having a first facial expression, identifying at least a second facial line on the subject having a second facial expression, the second facial line having at least one intersection with the first facial line, and injecting the injectable filler composition into a face of the subject at the at least one intersection.

In some embodiments, the method can further involve marking the first facial line on the face of the subject. In some embodiments, the method can further involve marking the first facial line and marking the second facial line on the face of the subject.

In some embodiments, the method can further involve identifying at least a third facial line in a third facial expression, the third facial line having at least one intersection with either or both of the first or second facial line; and injecting the injectable filler composition into the face of said subject at the at least one intersection that involves the third facial line.

In some aspects, the injectable filler composition can be injected proximal to a periosteum. In some embodiments, the injectable filler composition can be injected at a location of muscle attachment, muscle division, or muscle thinning. In some embodiments, the injectable filler composition can be injected at a location along a muscle such as, for example, *M. caninus, M. orbicularis oris, M. mentalis, M. indisivus labii inferioris, M. triangularis, M. buccinators*, or *M. masseter*. In some embodiments, the injectable filler composition can be injected at a jowl, a marionette line, a mental crease, an oral commissure and a *levator obicularis* fold. In some embodiments, the injectable filler composition can be injected into a mandibular area at a periosteum. In some embodiments, the injectable filler composition can be also injected into a mandibular area. In some embodiments the injection can be made intradermally. In some embodiments the injectable filler composition can be injected at a location of boney resorption as determined/revealed/exposed in animation.

In some aspects, about 0.10 cc of injectable filler composition can be injected into the face at an intersection of the second facial line with the first facial line. In some embodiments, between about 0.05 cc to about 1 cc of injectable filler composition can be injected into the face at an intersection of the second facial line with the first facial line.

In some embodiments, the first facial expression can be a pucker resting, anger, concentration, contempt, desire, disgust, excitement, fear, happiness, confusion, sadness, surprise, blank, frown, glare, laughter, pout, shock, smile, smirk, sneer, or snarl. In some embodiments, the facial expression can be a smile with a mouth having corners positioned as far upwards towards a forehead as possible. In some embodiments, the facial expression can be a smile with visible teeth and parted lips.

In some embodiments, the second facial expression can be a pucker, resting, anger, concentration, contempt, desire, disgust, excitement, fear, happiness, confusion, sadness, surprise, blank, frown, glare, laughter, pout, shock, smile, smirk, sneer, and snarl. In some embodiments, the second facial expression can be a frown that with a mouth having corners positioned as far up downwards toward a chin as possible. In some embodiments, the second facial expression can be a frown comprising a lip pout.

In some embodiments, a pucker has at least one facial feature such as pursed lips, sunken cheeks, a furrowed brow, or a wrinkled forehead.

In some embodiments, a first muscle that contracts in a first direction can be involved in forming the first facial expression and a second muscle that contracts in a second direction can be involved in forming the second facial expression, and the first and second directions can be at least partially opposing.

In some embodiments, the injectable filler composition can be a dermal filler that retains at least some of its three-dimensional shape after it is injected. In some embodiments, the injectable filler composition can be crosslinked. In some embodiments, the injectable filler composition does not swell up to greater than about 10% volume increase. In some embodiments, the injectable filler composition can be resistant to compression. In some embodiments, the injectable filler composition can be resistant to displacement.

In some embodiments, the injectable filler composition can contain a glycosaminoglycan. In some embodiments, the injectable filler composition can contain hyaluronic acid.

A method of teaching the application of an injectable filler composition to a face is disclosed in accordance with some aspects. In some embodiments, the method can involve: noting at least a first line on a first facial expression or representation thereof; noting at least a second line on a second facial expression or representation thereof; noting where the first and second lines intersect; and providing advice that one could administer an injectable filler composition at the intersect.

In some embodiments, the injectable filler composition can contain hyaluronic acid.

In some embodiments, the method can involve advising an individual that hyaluronic acid can be administered proximal to the periosteum. In some embodiments, the method can involve advising an individual that hyaluronic acid can be administered at a location in which there is a lack of volume under the subject's skin. In some embodiments, the lack of volume can be due to a lack of soft tissue or bone.

In some aspects, instructions for the application of an injectable filler composition to a face can be provided in printed material. In some embodiments, the instructions are provided in a digital format.

In some aspects, a method for administering an injectable filler composition to a subject is provided. The method includes identifying at least a first location on a face of a subject where there is an insufficient volume under the skin of the face of the subject, when the subject is expressing a first facial expression. The method further includes identifying at least a second location on the face of the subject where there is an insufficient volume under the skin of the face of the subject, when the subject is expressing a second facial expression. The method further includes injecting an injectable filler composition into the face of the subject at a location where the first and second locations overlap. In some embodiments, the injectable filler composition retains at least some of its three-dimensional shape after it is injected. In some embodiments, the injectable filler composition comprises a glycosaminoglycan and/or hyaluronic acid. In some embodiments, the injectable filler composition further comprises botulinum toxin. In some embodiments, the injection is intradermal. In some embodiments the first and second locations comprise tissue deficits. In some embodiments, the tissue deficit is a loss of bone, fat, connective tissue, or any combination thereof. In some embodiments, the first, second, or first and second location involves a tissue deficit due to muscle division, muscle thinning, or some combination thereof.

In some aspects, a method of applying a dermal filler to a face of a subject is provided. The method can include observing a subject's face in at least two different facial expressions and applying a dermal filler to at least one section of the subject's face that, during the at least two different facial expressions, appears to lack volume.

In some aspects, a method for identifying an under volume location is provided. The method can comprise identifying a first location where there is an insufficient volume under the skin of a face of a subject expressing a first facial expression, identifying a second location where there is an insufficient volume under the skin of a face of a subject expressing a second facial expression, and identifying where the first and second locations overlap, thereby identifying an area that lacks volume.

In some aspects, a method for identifying an area of skin that lacks volume beneath it is provided. The method can comprise identifying a first location on a subject's skin where there is an insufficient volume under the skin when the skin is arranged as a result of a first muscle being contracted, identifying a second location on the subject's skin where there is an insufficient volume under the skin when the skin is arranged as a result of a second muscle being contracted, and identifying where the first and second locations overlap, thereby identifying an area of skin that lacks volume beneath it. In some embodiments, the first location is not observable when the second muscle is contracted. In some embodiments, the second location is not observable when the first muscle is contracted. In some embodiments, the first muscle contracts in a direction that opposes the direction of contraction of the second muscle.

In some aspects, a method for ameliorating the adverse effects of aging on skin is provided. The method can comprise identifying at least a first location on a subject's skin where there is an insufficient volume under the subject's skin when wherein the subject's skin is arranged as a result of a first muscle being contracted. The method can further comprise identifying at least a second location on the subject's skin where there is an insufficient volume under the subject's skin when the subject's skin is arranged as a result of a second muscle being contracted. The method can further comprise applying a technique to an area of skin where the first and second locations overlap. The technique can increase the appearance of the volume of the skin, increase the appearance of the firmness of the skin, stimulate collagen production, increase the volume under the skin, or any combination thereof. In some embodiments, the technique comprises injecting an injectable filler into the subject. In some embodiments, the technique comprises applying energy to the area. In some embodiments, the energy comprises radio frequency energy.

In some aspects, a method for locating an area that is under volume in a subject's face is provided. The method can comprise identifying at least a first facial line on a subject having a first facial expression, identifying at least a second facial line on the subject having a second facial expression, and identifying a location where the first and second facial lines intersect.

In some aspects, a method for ameliorating the adverse effects of aging on skin is provided. The method can comprise identifying at least a first facial line on a subject having a first facial expression, identifying at least a second facial line on the subject having a second facial expression, and applying a technique to an area of skin where the first and second facial lines intersect. The technique can increase the appearance of volume of the skin, increase the appearance of firmness of the skin, stimulate collagen production, increase the volume under the skin, or any combination thereof. In some embodiments, the technique comprises injecting an injectable filler into the subject. In some embodiments, the technique comprises applying energy to the area of skin where the first and second facial lines intersect. In some embodiments, the energy comprises radio frequency energy.

In some aspects, a method for identifying an area that lacks volume in a subject is provided. The method comprises identifying at least a first wrinkle on a subject, wherein the wrinkle is present when a first muscle is contracted, identifying at least a second wrinkle on the subject, wherein the second wrinkle is present when a second muscle is contracted, and identifying a location where the first and second wrinkles intersect, said intersect denoting an area that lacks volume. In some embodiments, the first wrinkle is not present when the second muscle is contracted. In some embodiments, the second wrinkle is not present when the first muscle is contracted. In some embodiments, the first and second muscles contract in opposing directions. In some embodiments, the volume deficit appears to be superficial. In some embodiments, the volume deficit appears to be in the skin rather than beneath all of the layers of skin.

These and other embodiments are described in greater detail below.

Figure 1A:
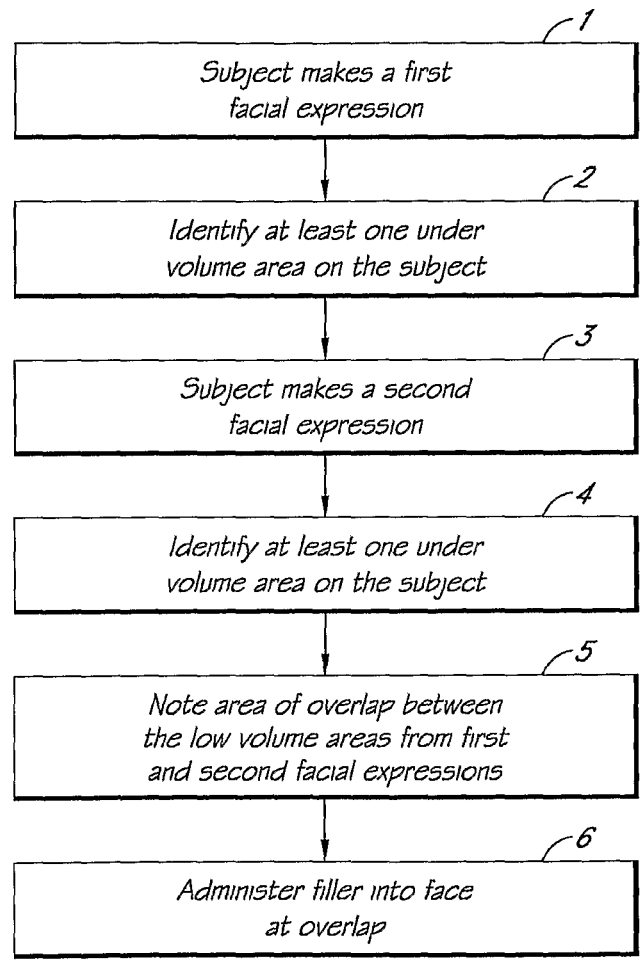
FIG. 1A depicts a flow chart depicting an embodiment involving the under volume dynamic injection technique.

Throughout the figures, the same reference numerals and characters, unless otherwise stated, are used to denote like features, elements, components or portions of the illustrated embodiments. Moreover, while the subject matter of this application will now be described in detail with reference to the figures, it is done so in connection with the illustrative embodiments. It is intended that changes and modifications can be made to the described embodiments without departing from the true scope and spirit of the subject invention as defined in part by the appended claims.

DETAILED DESCRIPTION OF THE PREFERRED EMBODIMENTS

It has been realized that the standard method of adding volume or firmness to a subject (for example, via the administration of injectable filler compositions), while adequate for many purposes, has various shortcomings. It has been appreciated that, rather than examining or considering the face as a static object, and using static features to guide one in the application of a dermal filler, a more dynamic approach can be taken.

In some embodiments, in order to determine where to place an injectable filler in a subject, a comparison of the subject's face is made while the subject makes various facial expressions. In some embodiments, the method includes identifying areas or locations that appear to lack volume or are "under volume" in a subject while the subject expresses at least two different facial expressions. One can then determine where those areas or locations of under volume overlap. The dermal filler can be applied to those areas of overlap in order to obtain beneficial results.

In some embodiments, the method for determining where to place an injectable filler employs identifying a first set of lines or wrinkles in a subject's face when the subject's face is in a first expression, identifying a second set of lines or wrinkles in the subject's face when the subject's face is in a second expression, identifying where at least one of the lines from the first set intersects with a line from the second set, and injecting the filler using the intersection points as guideposts for the injection.

It has also been appreciated that many traditional techniques do not take full advantage of the characteristics of volumetric fillers. Thus, some of the disclosed embodiments are useful in allowing one to determine where and how fillers, including volumetric fillers, can be applied.

Some embodiments of the techniques provide for a superior distribution of an injectable filler in a subject. In some embodiments, the distribution is more effective in targeting areas that result in a desirable change. In some embodiments, the technique results in less pain to the subject. In some embodiments, the method allows for faster application of the injectable filler. In some embodiments the added filler looks more natural even when the subject's face is animated.

In some embodiments, the dynamic injection technique is amenable to the training of those that would like to apply the injectable filler. This can allow for the ready dissemination and standardization of the technique, as well as other advantages. These, and additional aspects, are discussed in greater detail below.

The present description first describes various terms used in describing various aspects described herein. A general description of various embodiments of the administration methods is then provided and is followed by a more detailed description of specific aspects of the methods and variations. An additional section regarding additional embodiments is then provided. Finally, examples of using the various methods are disclosed.

Definitions

"Injectable filler composition" includes a composition that can be administered through injection into or beneath the skin of a subject. The injectable filler composition should not be unduly problematic for the subject receiving the composition. As will be appreciated by one of skill in the art, there are a large number of compositions that can be used as a filler for various embodiments disclosed herein. In some embodiments, the fillers are dermal fillers. In some embodiments, the filler is selected from RESTYLANE™ and PERLANE® dermal fillers. Examples of fillers include those disclosed in U.S. Pat. Nos. 5,633,001, 5,007,940, 5,827,937, 5,128,326, 5,399,351, and 5,143,724, as well as PCT Pub. No. WO 87/07898, all of which are herein incorporated by reference in their entireties. In some embodiments, the composition is a cross-linked biocompatible polysaccharide gel composition. In some embodiments, the composition is formed by forming an aqueous solution of a water soluble, cross-linkable polysaccharide; initiating a cross-linking of said polysaccharide in the presence of a polyfunctional cross-linking agent; sterically hindering the cross-linking reaction from being terminating before gelation occurs, an activated polysaccharide thereby being obtained; and reintroducing sterically unhindered conditions for said activated polysaccharide so as to continue the cross-linking thereof up to a viscoleastic gel.

In some embodiments, the injectable filler is characterized by its source. In some embodiments, the source can be biologic and/or synthetic. Biologic injectable fillers can be those that are derived from a living organism. Synthetic injectable fillers can further be divided into two groups, a) man-made fillers for which there is no biologic equivalent and b) man-made substances for which there is an equivalent biologic. In some embodiments, the injectable filler can be characterized by the body's ability to clear a product without external intervention (e.g., these can be biodegradable or nonbiodegradable).

Examples of biologic, biodegradable fillers are those that include materials derived from organism, human, and/or animal tissues and/or products. Examples of such fillers include the following: hyaluronic acid (HA), (such as the following: avian HA, bovine HA, and human HA (e.g., RESTYLANE™ injectable filler)) and collagen (such as collagen I, collagen II, collagen III, crosslinked and/or noncrosslinked, bovine, porcine, human, and autologous collagen. Additional examples of collagen based fillers include ZYPLAST™ (collagen derived from bovine tissue), ZYDERM I™ (collagen derived from bovine tissue), ZYDERM II™ (collagen derived from bovine tissue), EVOLENCE™ (porcine derived collagen), and FIBREL™ (porcine derived collagen). As will be appreciated by one of skill in the art, in some embodiments, the injectable filler is self-replicating, and can include living cells (such as collagen-producing cells or fibroblasts). Thus, in some embodiments there are injectable fillers that are biological and are relatively long lasting or relatively "permanent."

Synthetic, biodegradable, injectable fillers include RADIANCE™ and RADIESSE™ (microspheres of at least calcium and phosphate ions) injectable fillers, polyacids and polyethers described in U.S. Pat. No. 7,192,984 (e.g., carboxymethyl cellulose (CMC) and polyethylene oxide), and LARESSE™ (polymer, polyacid, and/or polyether, similar but not identical to HA type molecules).

Synthetic, non-biodegradable, injectable fillers include injectable fillers that are not readily broken down in the body. Synthetic, non-biodegradable, injectable fillers can include injectable fillers that include a biologic component (and vice versa). In some embodiments, at least a portion of product cannot be significantly broken down by various body processes. Additional examples of synthetic non-biodegradable fillers include the following: ARTEFIL™ (polymethylmethacrylate (PMMA) microspheres suspended in bovine collagen), ARTECOL™ (polymethylmethacrylate (PMMA) microspheres suspended in bovine collagen), polymethylmethacrylate (Plexiglas) in bovine collagen carrier, denatured, silicone, and various polymers, polyacids, and polyethers. In some embodiments, the carrier has rapid biodegradation. Of course, as will be appreciated by one of skill in the art, in some embodiments, any one, combination, or ingredient of the above fillers can be combined with the other fillers (or alternative fillers) in various embodiments and for particular results.

As will be appreciated by one of skill in the art, injectable fillers need not be categorized by both their source and their ability to stay or be cleared from the body. That is, some fillers can simply be biological, synthetic, biodegradable, or non-biodegradable. Additionally, as will be appreciated by one of skill in the art, some injectable fillers can include parts or aspects of various combinations of the above or following substances.

Examples of injectable fillers include a substance selected from the following: collagen, fat, human or animal derived collagen, bovine collagen, type I collagen, type II collagen, type III collagen, 3.5% bovine dermal collagen cross-linked by glutaraldehyde to form a latticework, natural human collagen, autologous collagen, polymethylmethacrylate microspheres (optionally suspended in bovine collagen), suspension of collagen fibers prepared from the patient's tissue, human tissue collagen matrix derived from cadaveric dermis, the polyacids and polyethers described in U.S. Pat. No. 7,192,984 (e.g., carboxymethyl cellulose (CMC) and polyethylene oxide), acellular human cadaveric dermis that has been freeze-dried, micronized acellular human cadaveric dermis that has been freeze-dried, cultured autologous fibroblasts, hyaluronic acid, non-animal-stabilized hyaluronic acid derivative, microspheres of calcium hydroxyl appetite suspended in an aqueous gel carrier, dextran beads suspended in hylan gel of nonanimal origin (e.g., 40- to 60-μm in diameter), solubilized elastin peptides with bovine collagen, silicone, solubilized elastin peptides with bovine collagen, poly-L-lactic acid, Gore-Tex (PTFE), glycosylated collagen, PMMA, bone-forming calcium apatite, cultured human cells, expanded polytetrafluoroethylene (e-PTFE), SOFTFORM® of ePTFE, and some combination thereof. Further examples of injectable fillers include the following: AQUAMID® (comprising water and cross-linked polymers), ARTEFIL® (polymethylmethacrylate (PMMA) microspheres suspended in bovine collagen), LARESSE® Dermal Filler (synthetic, biocompatible polymers, non-HA gel comprising absorbable medical polymers), ARTECOLL® (polymethylmethacrylate (PMMA) microspheres suspended in bovine collagen), BELOTERO®, BIO-ALCAMID™ (synthetic reticulate polymer (poly-alkyl-imide), CAPTIQUE™ (non-animal hyaluronic acid), COSMODERM™ (human collagen skin filler), COMOPLAST™, CYMETRA®, autologen, DERMALOGEN®, FASCIAN™ (fascia), fascia, fat, HYLAFORM™ (avian hyaluronic acid), JUVEDERM® (biosynthesized, non-animal hyaluronic acid), RADIESSE™ (microspheres of at least calcium and phosphate ions), SCULPTRA® (poly-L-lactic acid (PLLA)), collagen, hyaluronic acid, RESTYLANE™, PERLANE®, ZYDERM®, ZYPLAST® (collagen derived from bovine tissue), DERMALIVE®, (hyaluronic acid and acrylic hydrogel particles), DERMADEEP® (hyaluronic acid and acrylic hydrogel particles), HYDRAFILL®, ISOLAGEN® (cultured autologous human fibroblasts), LARESSE™ (carboxymethylcellulose (CMC) and polyethylene oxide (PEO) filler), PURAGEN™ (filler comprising double cross-linked hyaluron molecules), REVIDERM® INTRA (filler comprising flexible DEXTRAN micro-beads suspended in super-coiled, stabilized hyaluronic acid), SCULPTRA™ (Formerly NEW-FILL™, filler from poly-L-lactic acid), Teosyal, SURGIDERM® (hyaluronic acid filler involving 3D hyaluronic acid matrix technology), OUTLINE®, ANIKA®, Cosmetic tissue augmentation (CTA, from ANIKA), and combinations thereof.

As will be appreciated by one of skill in the art, any of the above fillers or components thereof can include other materials, for example, anesthetic materials, including, without limitation, lidocaine, prilocaine, tetracaine, etc.

"Volumetric filler" is a type of injectable filler composition. Volumetric fillers can be dermal fillers. In some embodiments, the volumetric filler is capable of crosslinking and/or is crosslinked. Crosslinked compositions allow the filler to have predictably no or minimal volume or substance loss on injection. In some embodiments they also provide predictable expansion or "swelling" with re-hydration on injection: swelling to no more than 10% volume increase; not "shrinking" or losing volume as some fillers that lose water uncrosslinked HA volumes; and/or have sufficient tensile compression resistance. In some embodiments, the volumetric filler involves microbead technology (e.g., as disclosed in U.S. Pat. Nos. 5,633,001 and 5,007,040, herein incorporated by reference in their entireties). In some embodiments, this allows compression resistance. In some embodiments this allows for the composition to have the ability to resist displacement. Other fillers, described as "slurries," can be used but can be prone to displacement (e.g., disclosed in U.S. Pat. Nos. 5,143,724, 5,633,001, herein incorporated by reference in their entireties). In some embodiments, the filler has the biocompatibility and "feel" of tissue rather than boney implants or sedimentary products that can feel hard. However, bony implant or sedimentary fillers can also be used in some embodiments.

"Dermal filler" is a type of injectable filler composition. Dermal filler denotes that the filler is compatible for use in or under the skin. Dermal fillers can be volumetric fillers.

"Opposing" in reference to a second direction denotes that when something moves in a first direction, at least one vector or component of the movement in the second direction is more than ninety degrees from at least one vector or component of the movement in the first direction. Thus, forces in or movement of the skin need not be 180 degrees between the first and second expression to be opposing.

"Expression," as in facial expression, can denote a wide range of configurations of the face or other area of skin on a subject. In some embodiments, this can be selected from the following: pucker, resting, anger, concentration, contempt, desire, disgust, excitement, fear, happiness, confusion, sadness, surprise, blank, frown, glare, laughter, pout, shock, smile, smirk, sneer, snarl, and some combination or subparts thereof. However, as will be appreciated by one of skill in the art, these terms can simply be useful in communicating various desired facial instructions to the subject. As will be appreciated by one of skill in the art, it is not critical that the subject express a full or formally recognized facial expression, but that the similarities or line intersections that occur from one facial configuration to another be identified. As such, "expression" includes fully recognized expressions (such as those noted above), partial expressions, as well as when individual muscles or muscle groups are used in informal configurations of the face. Thus, in some embodiments, a "first expression" can include a situation in which only a single muscle is being contracted, and indeed, in situations in which the face is resting, it would include a situation where no muscle is being contracted. When a full facial expression is meant to be required, it can be referred to as a "complete facial expression" or "standard facial expression." If the language of the instructor fails to be understood by the patient and the desired expression is not demonstrated, the instructor/injector may have the patient say certain letters of the alphabet instead of making expressions.

Additionally, as will be appreciated by one of skill in the art, many embodiments in the present technique can be applied to various locations across a subject's body. Thus, even though the term "expression" is used, it does not require that this only be applicable to the face or head area of a subject. Rather, it refers to at least two differing arrangements in which the skin and/or muscles are in different states. Thus, for example, a neck, back, leg, elbow, knee, hand, etc. can be put through various "expressions."

"At the intersection" or "at a location" denotes that these locations are targets that indicate generally where filler should be administered. As will be appreciated by one of skill in the art, these targets generally indicate where the filler should be deposited; thus, the actual insertion of the needle or other administration device need not pass through this intersection or target. Similarly, in some embodiments, one can inject near a location and then massage the injectable composition closer to the target area.

"Marked" or "traced" generally mean that the line, wrinkle, or area or location at issue has been indicated as present on a subject. Generally this can include taking a pin and highlighting or indicating where the item or indicator of interest is while the face is in one expression. As will be appreciated by one of skill in the art, one need not trace the indicator completely, or even precisely trace over it. In some embodiments, all that needs to occur is that the mark or trace allows one of skill in the art to recognize where the line is across the various expressions or states of the face.

"Under," "on," "in," or similar term, in reference to an area that lacks volume for a subject's skin does not strictly require that the lack of volume be under the skin (e.g., bone) or be limited to those sections that are only within the skin or formally part of the skin (unless the context of the disclosure requires otherwise). As will be appreciated by one of skill in the art, the lack in volume can be due to anything underneath the outermost layer of skin. Thus, "under the skin", when used in reference to the under volume or insufficient volume areas will typically include all but the outer most layer of skin cells (e.g., most of the depth of skin, as well as bone). Similarly, an "insufficient volume in the skin" (unless explicitly denoted otherwise) will also include a lack of volume due to aspects that are under the skin (e.g., bone loss). Similarly, identifying an area "on" a subject's skin simply denotes that an area on the surface of the skin is observed or identified, and it does not require that the cause of the lack of volume be limited purely to the skin. Similarly, "an area of skin that lacks volume beneath it" can lack volume due to a lack cells beneath the outermost layer of skin cells. As such, it can include deficits due to skin and/or bone, etc. Thus, "skin," in this context, can generally be interpreted to mean the outermost layer of cells of the subject's skin, rather than the entire depth of the organ (unless explicitly denoted otherwise).

In some embodiments, if animation reveals a deficit (lack of volume, line, wrinkle, etc) in one positioning, and a second deficit (lack of volume, line, wrinkle, etc) is revealed at rest or in animation, but the second deficit has been caused by a trauma or injury, the intersection or overlap between the two areas can also constitute an identified location for filler placement or firming treatment. In some embodiments, deficits caused by trauma or injury are excluded from the process.

The term "indicator" refers to wrinkles, lines, under volume areas, etc., which are looked at in each separate state or facial expression. Informed by the guidance provided herein, one of skill in the art will readily be able to identify these areas. The point of intersection of the indicators is referred to as an intersection point, areas of overlap, etc.

In some embodiments, the method is used to alter the appearance of a subject's face. In some embodiments, this alteration is purely an aesthetic alteration. In some embodiments, the alteration does not treat or adjust any deformity that the subject may have. For example, in some embodiments, the subject may simply want added volume to various areas of their face. As such, the application of filler will not necessarily be considered a treatment of the subject's face in all embodiments. Additionally, the term "under volume" does not imply or require that there is necessarily a deformity in the subject's face. Rather, it simply denotes that there appears to be less volume under the skin in one area than in another. In some embodiments, the filler and technique is applied as a treatment of a deformity in a patient. Such applications can be more specifically denoted by the recitation of the fact that a "deformity" is being "treated," or by the fact that the subject is called a "patient." Applications in which no deformity is being addressed can be more specifically denoted by the use of the terms "non-treatment," "subject-preference" or similar term. When such terms are not explicitly used, the techniques and aspects are generic to both treatment and non-treatment applications. As will be appreciated by one of skill in the art, the term "subject" encompasses "patient."

Dynamic Injections

As noted above, some of the presently disclosed embodiments are directed to a method of administering an injectable filler to a subject's face. As described in detail below, some of these embodiments involve making observations and comparisons between at least two facial expressions on a subject's face. Specific indicators in the various facial expressions are noted, as are their relationship to one another, and these are used as guideposts for administering the injectable filler.

FIG. 1A is a flow chart of one embodiment of a method of administering an injectable filler to a subject's face by using a dynamic injection technique. As noted above, in some embodiments, this involves first having the subject make a first expression 1. While the subject is expressing the first expression, one identifies at least one area on the subject's face that appears to be, relatively speaking, under volume 2. This area can be denoted as a first area. Next, one has the subject make a second facial expression 3. While the subject is expressing this second expression, one identifies at least one area on the subject's face that appears to be, relatively speaking, under volume 4. This under volume area that is apparent in the second expression can be denoted as a second area. Following this, one identifies where the first and second areas overlap. That is, one identifies those areas, or subparts thereof, where there was, relatively speaking, an apparent lack of volume during both of the expressions 5. Following this, one administers an injectable filler to the subject where the first and second areas or locations overlap 6. As will be appreciated by one of skill in the art, the above process can be repeated multiple times, identifying numerous overlapping areas, each of which, as described above, can be dealt with. Alternatively, only those areas that are under volume between multiple facial expressions are injected. For example, in some embodiments, only those areas that are under volume in at least 3, 4, 5, 6, 7, 8, 9, 10, 11, 12, 13, 14, 15, 16, 17, 18, 19, 20 or more facial expressions are injected. Additionally, as will be appreciated by one of skill in the art, not every area from the first expression will overlap with every, or any, area from the second expression. A sufficient amount of injectable filler composition can be added to make the location of even height or desirable height (e.g., fullness and/or volume) with the surrounding tissue (e.g. skin).

Figure 1B:
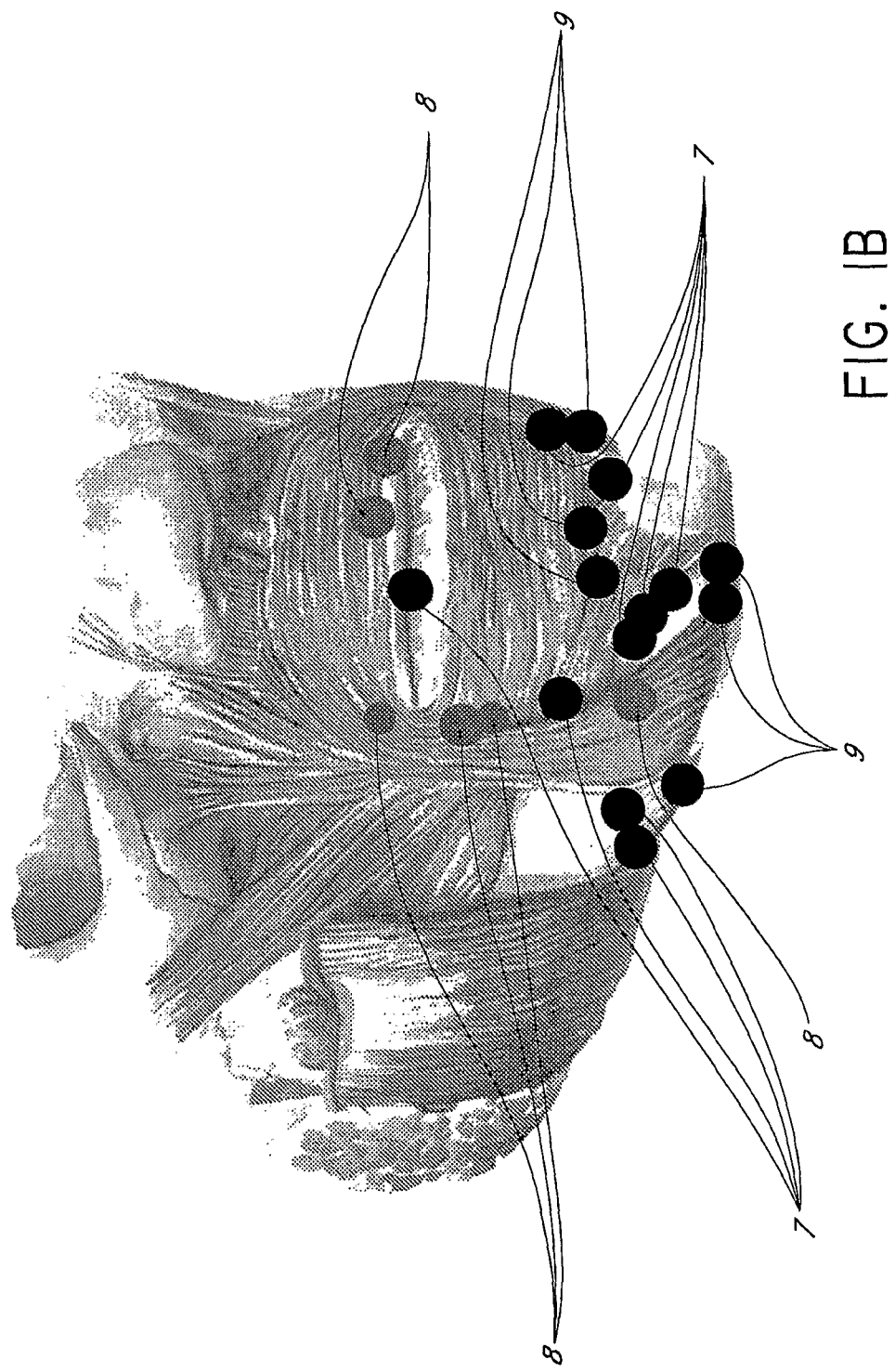
FIG. 1B is a depiction depicting areas that can be under volume.
Figure 1C:
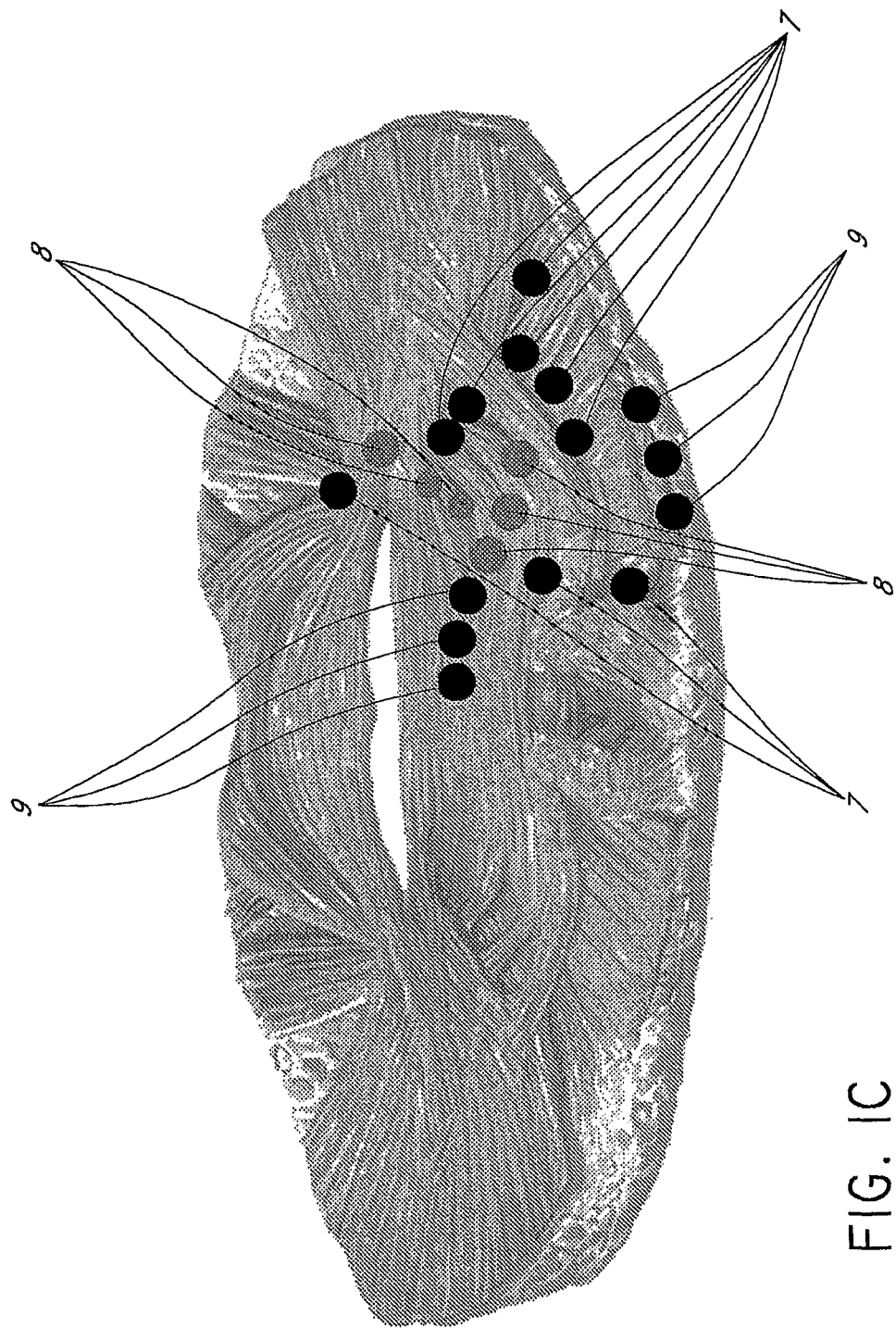
FIG. 1C is a depiction depicting areas that can be under volume.
Figure 2:
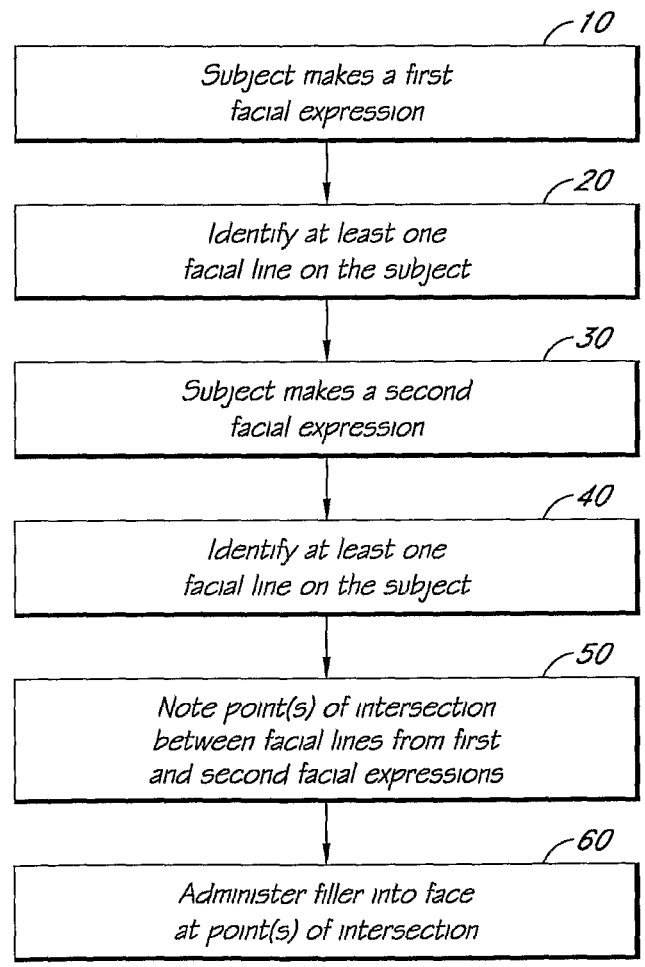
FIG. 2 depicts a flow chart depicting an embodiments of a grid based dynamic injection technique.

As will be appreciated by one of skill in the art, in some embodiments, there can be certain areas of the face that are especially prone to being under volume across various people. Examples of these areas are shown in FIG. 1B and FIG. 1C. As will be appreciated by one of skill in the art, these areas need not always be under volume; however, they provide an excellent initial point to start examining a subject's face. Additionally, the types of features that are shown in the Figures can also result in areas that appear to lack volume elsewhere. Thus, areas between muscles 7, areas in which cross pull (or opposing pull) due to animation occur 8, and areas or points of attachment 9 can all be areas to initially examine during the above or following methods. FIG. 1B and FIG. 1C demonstrates these three areas In some embodiments, the dynamic injection technique is, relatively speaking, directed by more specific facial features. For example, the embodiment depicted in flow chart in FIG. 2 is a grid-based system. As used herein, the term "grid" refers to at least one point of intersection. Typically, this point of intersection is between at least two lines, if not more, where the lines are present in varying facial expressions. While the technique in FIG. 2 is similar to the technique in FIG. 1A, in that it uses at least two different facial expressions to assist in identifying specific areas to be injected, the technique in FIG. 2 uses specific facial features to guide the person applying the injectable filler composition. As shown at step 10, a subject makes a first facial expression. A first facial line(s) (which can include a wrinkle) can be identified 20 on the subject making the first facial expression. In some embodiments, the first facial line(s) can be, but need not be, marked. Ways of marking the facial lines are described in further detail below, but can include tracing the lines on the subject's face with a marker. Next, the subject makes a second facial expression 30. A second facial line(s) associated with the second facial expression can be identified 40. As with the first facial line(s), the second facial line(s) can also, but need not be, marked. The subject can make any number of additional facial expressions, and the associated line(s) can be identified. Point(s) of intersection between the first and second facial lines from each of the facial expressions can be identified 50. In some embodiments, the points of intersection can be, but need not be, physically marked. An injectable filler is administered to the face of the subject at or using the point(s) of intersection 60. As will be appreciated by one of skill in the art, the subject can make the facial expressions on their own, or be instructed to make one or more facial expressions by someone else, such as the person applying the injectable filler composition. Additionally, the person administering the filler can also assist the subject in making the facial expression(s), e.g., manually manipulating the face/skin. In some embodiments, this assistance or manual manipulation of the skin is done to facilitate the contraction of the muscles. By adding this additional force to the skin (e.g., by adding additional pressure to the skin) additional folds, lines, and/or defects can be revealed that simple animation does not reveal. In some embodiments, this is simply done by moving the skin in the same or similar manner that a muscle in the subject would move (e.g., contract) the skin in. In some embodiments, the manual manipulation of a subject's face by a nonsubject simply assists the subject's muscles. In some embodiments, the manual manipulation of a subject's face by a nonsubject is performed without the subject moving the subject's face. Regardless, the wrinkles, lines, or areas of insufficient volume revealed and/or induced by the manual manipulation can be used as described herein. In some embodiments, the only wrinkles, lines, and/or areas of insufficient volume that are examined are those that occur when the subject makes a facial expression or muscle contraction on his own (e.g., without the assistance of a nonsubject).

Figure 3A:
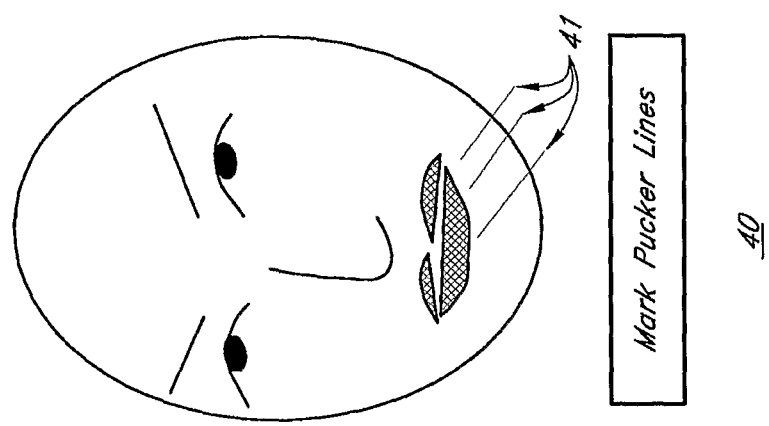
FIG. 3A is a facial representation in which a first and then as second set of lines have been traced.
Figure 3A:
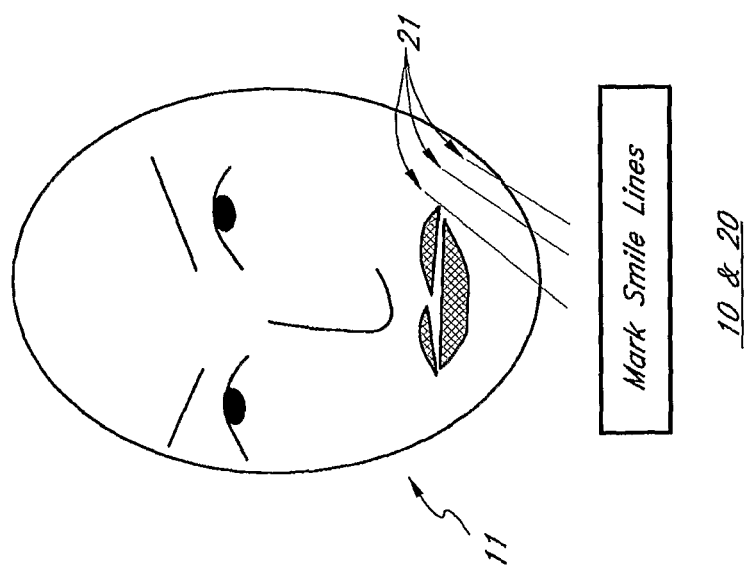
Figure 3B:
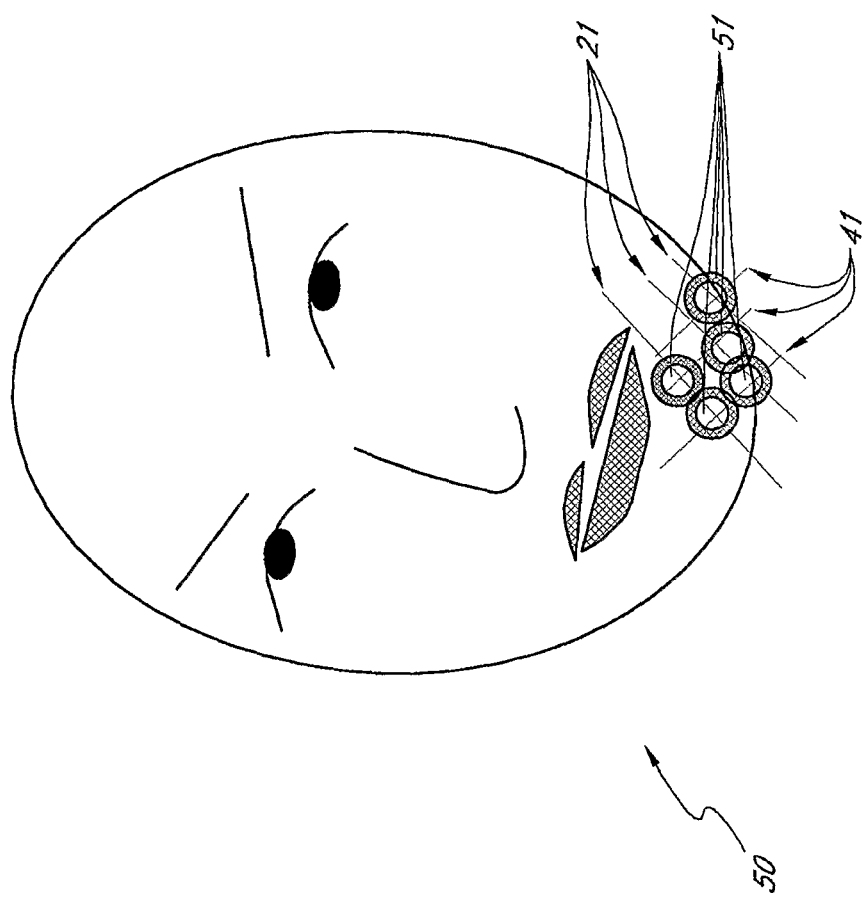
FIG. 3B is a facial representation in which the intersection marks have been noted or identified

The steps in the flow chart in FIG. 2 are depicted as applied to a representation of a face in FIG. 3A to FIG. 3E. In the left-hand side of FIG. 3A, the subject makes a first expression 11 as a first step 10. A first set of lines 21 is identified 20 in the subject's first facial expression. The subject then makes a second facial expression (not depicted) as a third step 30 and a second set of lines 41 is identified 40 in the subject's second facial expression (right-hand side of FIG. 3A). As shown in FIG. 3B, one then identifies 50 the points of intersection 51 of the sets of lines 21 and 41.

Figure 3C:
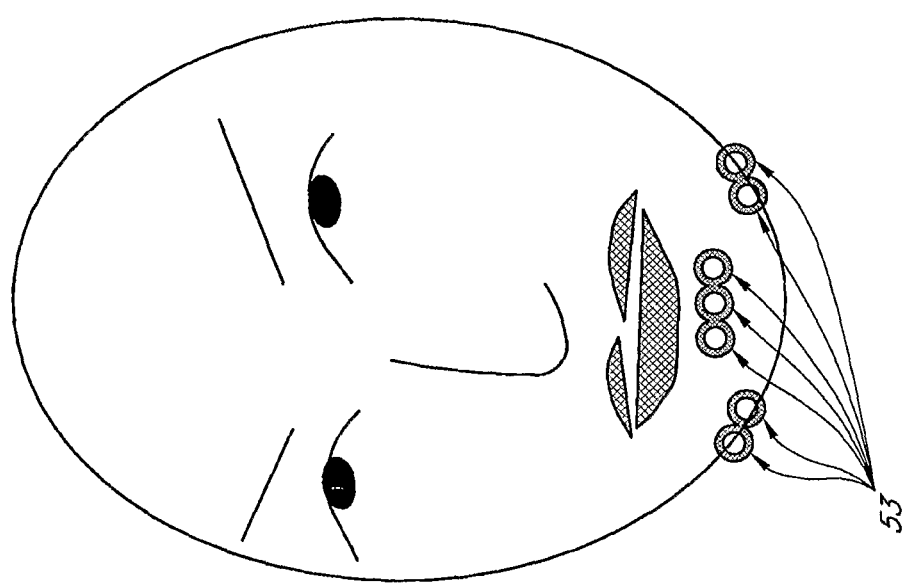
FIG. 3C is a facial representation in which additional points of injection or treatment, relating to points of attachment, have been noted.

As an optional step, one can identify points of attachment 53 that could benefit from added volume by having the subject make a "pouting" or pouting frown expression, as shown in FIG. 3C (expression not shown).

Figure 3D:
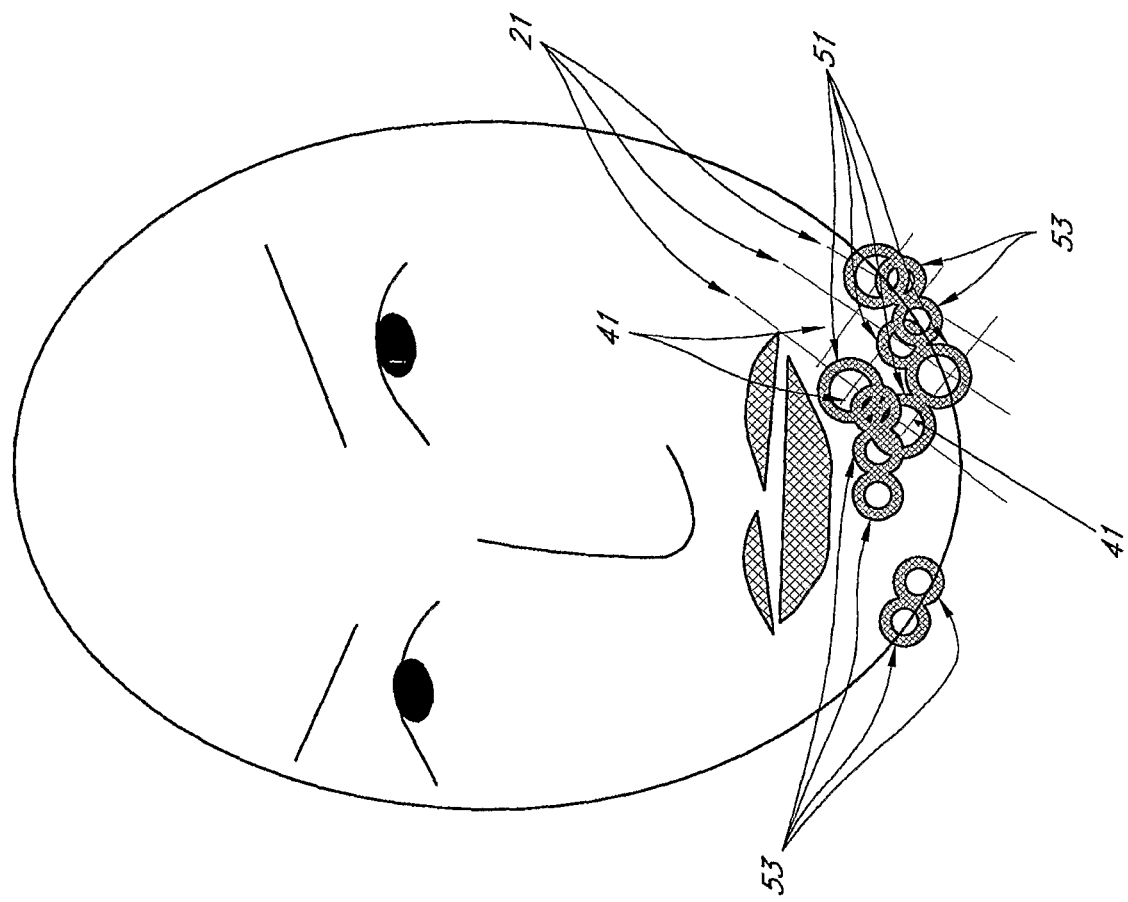
FIG. 3D is a facial representation in which all of the above noted points of injection or treatment are indicated.

Next, in step 60 as depicted in FIG. 3D, one can inject the injectable filler composition into those areas that have been identified above. In some embodiments, one injects a bolus of the injectable filler composition near each circled point at about a 90-degree injection angle, after aspirating. In some embodiments, one avoids blood vessels and foramen. One can add a sufficient amount of injectable filler composition to raise the identified location to the level of the surrounding area. In some embodiments, intradermal injections are used in areas where firming is desired and/or where wrinkle adjustment occurs over the foramen and/or larger vessels. Following this, one can have the subject animate the subject's face to ensure that the injections were effective. If required, the above steps can be repeated until the desired result is achieved.

Figure 3E:
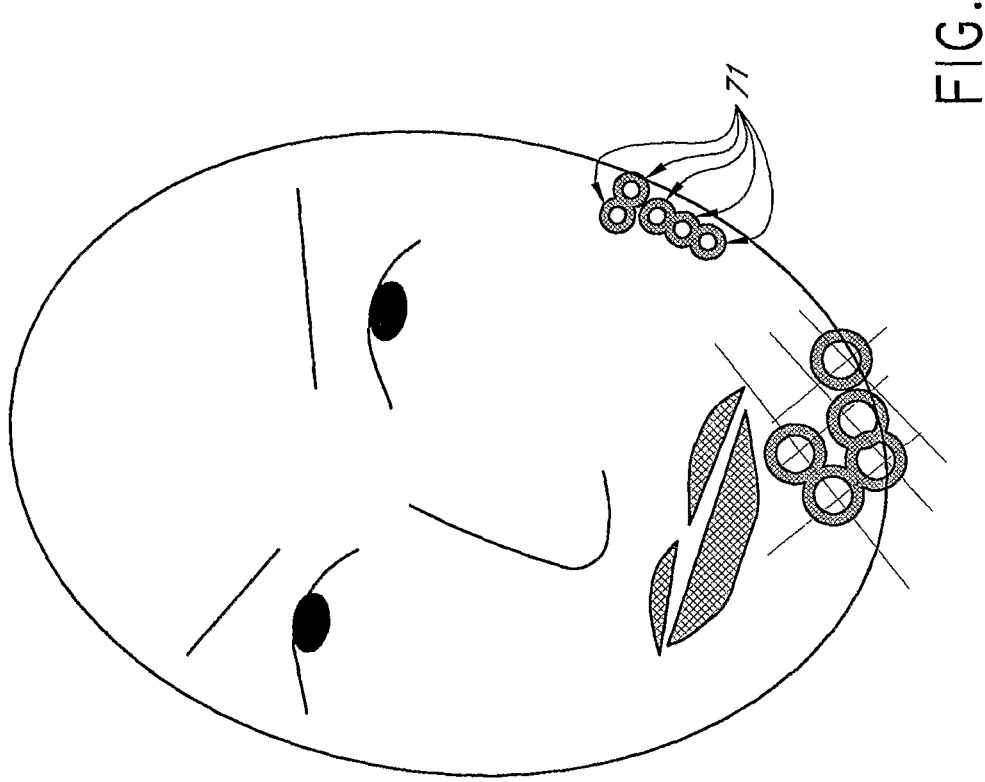
FIG. 3E is a facial representation in which additional, optional points of injection or treatment are noted.

In some embodiments, additional steps can also be performed to provide additional benefits through the application of additional volumetric fillers. For example, FIG. 3E depicts one optional step 70, in which additional injections are made at locations 71 along the jaw line to smooth the face at rest and in animation. These injections can add volume to redrape the skin over lower face structures. The injections can be intradermal or at the periosteum as the specific anatomy allows or dictates.

In some embodiments, the injection is done while the subject is in a sitting position. The facial expression can be made while the subject is in the sitting position, and the injections can be performed while the subject remains in the same sitting position.

A wide variety of facial expressions can be used with the various embodiments disclosed herein. In some embodiments, the facial expression can be a pucker, resting, anger, concentration, contempt, desire, disgust, excitement, fear, happiness, confusion, sadness, surprise, blank, frown, glare, laughter, pout, shock, smile, smirk, sneer or snarl. In some embodiments where the facial expression is a smile, the smile can have a mouth having corners positioned substantially upwards, e.g., as far upwards towards a forehead as possible or as the subject is reasonably able. In some embodiments where the facial expression is a smile, the smile can have a mouth having visible teeth and parted lips. In some embodiments where the facial expression is a frown, the frown can have a mouth having corners positioned substantially downwards, e.g., as far downwards toward a chin as possible or as the subject is reasonably able. In some embodiments where the facial expression is a pucker, the pucker can have pursed lips, sunken cheeks, a furrowed brow, a wrinkled forehead, or any combination thereof.

In some embodiments if the patient is confused by the "expression" of animation, the opposing expressions may be demonstrated by having the patient repeat phrases that mimic the expression line, and/or repeat letters of the alphabet that do the same. In some embodiments the patient is instructed to speak, using opposing motions of speech to mimic expressions.

The second and any subsequent facial expressions can be made in a different direction from the first facial expression. In some embodiments, the second or subsequent facial expression is made moving at least one section of skin in an opposing direction from the first facial expression. In some embodiments, the second or subsequent facial expression is an opposite facial expression from the first facial expression. For example, in some embodiments where the first facial expression is a smile, the second facial expression may be a frown. In some embodiments, any subsequent facial expressions are at least partially different from the first facial expression. As noted above, a complete or formal "expression" need not be required in every embodiment. As will be appreciated by one of skill in the art, if local adjustments are desired, then only parts of the face can be moved through the various expressions. In some embodiments, the initial expression is the face at rest. In some embodiments, all or at least two of the expressions involve at least some muscles being contracted. As will be appreciated by one of skill in the art, although the "dynamic" injection technique or "animated" injection technique described herein involves at least two different states of a location of skin, the actual injection does not need to be, and preferably is not, performed while the subject's skin or face is animated. In some embodiments, the subject's face is injected when the subject's face is at rest. In other embodiments, the subject's face is injected in either the first or second facial expression. In some embodiments, the subject's face is injected when the subject's face is in a new facial expression that is different from those expressions used to determine the location of injection.

In some embodiments, the facial lines or wrinkles on or associated with a facial expression can, but need not, be marked. Marking can be accomplished by a wide variety of methods. In some embodiments, the face is physically marked. The physical marking can be made using, for example, a pen, pencil, crayon, marker, ink, clay, paint, chalk, makeup, cosmetic, tape, indentation, and the like. In some embodiments, the marking is made using washable ink. The marking can be made using a combination of colors, a single colored (including black) marking, or colorless textured mark visible by shadow, shine, or shape. In some embodiments the mark may be made by "drawing" through topically applied cream, lotion, gel, etc. In some embodiments, the facial lines from a first facial expression can be made using one color and the facial lines from a second facial expression can be made using a different color.

In some embodiments, an image of the facial expression can be taken or made. The image can be taken or made using a variety of methods. In some embodiments, the image can be taken or made using a sketching, a camera, a video camera, or a mold. In some embodiments, the images can be marked to indicate facial lines on or associated with the facial expressions. In some embodiments, the image of a first facial expression can be superimposed on the image of any subsequent facial expressions, thereby allowing intersecting lines or wrinkles to be identified.

Points of intersection between any of the facial lines from any of the facial expression can be noted. In some embodiments, the points of intersection can be marked. In some embodiments, the points of intersection can be marked using a circle, an X, or a dot.

A wide variety of filler compositions can be used with the various embodiments disclosed herein. In some embodiments, the filler composition is a flowable substance such as a suspension, liquid or slurry. In some embodiments, the substance is one that can be used in cosmetic applications. In some embodiments, this can be a dermal filler, such as RESTYLANE® dermal filler. In some embodiments, the filler composition is a dermal filler and retains at least some of its three-dimensional shape after it is injected. In some embodiments, the filler composition is crosslinked. See, U.S. Pat. No. 5,827,937, which is hereby incorporated by reference in its entirety. The filler composition can be resistant to swelling. In some embodiments, the filler composition does not swell up to greater than about 10% volume increase. The filler composition can be resistant to compression. The filler composition can be resistant to displacement. The filler composition can be a biocompatible material. The filler composition can contain a glycosaminoglycan. The filler composition can contain or be hyaluronic acid. In some embodiments the filler composition comprises botulinum toxin, e.g., botulinum toxin A.

In some embodiments, the subject can receive anesthesia prior to administration of the filler composition. However, in some embodiments, injectable anesthesia is avoided to decrease risk of anesthesia-associated temporary paralysis, asymmetry and/or swelling. In some embodiments, a nerve block is not used for the injection procedure. In some embodiments, any anesthesia used does not alter the movement or ability of the subject to move their facial muscles.

In some embodiments, the filler composition is administered at a location in which there is a lack of volume under the subject's skin. This can be due to, for example, a lack of soft tissue or bone. In some embodiments, the filler composition is administered at a location of deficit identified by the grid, as described above.

In some embodiments, the administration can be done by injection. The filler composition can be injected proximal to a periosteum. In some embodiments, the injectable filler is injected at and/or between the periosteum and the dermis. In some embodiments, the filler is at least provided (or injected to or at) the superficial subcutis. In some embodiments, the injection occurs at or above the periosteum. In some embodiments, the injection occurs at or near the subcutis layer. In some embodiments, the injection is into the dermis. In some embodiments, the injectable filler is injected supraperiosteally. In some embodiments, the filler is at least provided (or injected to or at) the deep dermis. In some embodiments, the injection of the filler composition can be at the periosteum in positions of muscle attachments, muscle divisions, muscle thinning or combinations thereof. In some embodiments, the filler composition can be injected at a location of muscle attachment, muscle division, muscle thinning, or any combination thereof. In some embodiments, the filler composition can be injected at a location along a muscle, including *M. caninus, M. orbicularis oris, M. mentalis, M. indisivus labii inferioris, M. triangularis, M. buccinators*, and *M. masseter*, or any combination thereof. In some embodiments involving the perioral musculature, the filler composition can be injected at points between muscles, such as the drop between *M. buccinator* and *M. masseter; M. triangularis* and *M. buccinators, M. triangularis* and *M. incisivus labii inferioris, M. mentalis* and *M. incisivus labii inferioris, M. orbicularis oris* and *Pars alaris m. nasalis*, or *M. orbicularis oris* and *M. mentalis*. The filler composition can be injected along locations of muscle cross-pull, such as along *M. caninus* or *M. orbicularis oris*, or any of the other muscles listed above. The filler composition can be injected at points of attachment of *M. caninus, M. orbicularis oris, M. mentalis, M. indisivus labii inferioris, M. triangularis, M. buccinators*, and *M. masseter*, or any combination thereof.

In some embodiments, the injectable filler composition can be injected at a location selected from one or more of a jowl, a marionette line, a mental crease, an oral commissure and/or a *levator obicularis* fold.

In some embodiments, the injection can be made supraperiosteal. In this case, the needle is inserted at about a 90-degree angle to the face. Injection can be performed by serial puncture, threading, or tanning. The injections can be intradermal or at the periosteum as specific anatomy allows or limits. The injections can be deep injections. Deep injection reduces the burden of the skin to contain the implant and improves volume benefits of the implant. In some embodiments the injections are as an inverted cone technique.

In some embodiments, the injection can be used to place boluses at points of facial line intersection. In some embodiments, the injection can be used to place boluses at points of deficit. In some embodiments, the points of deficit can be identified, for example, using the grid technique. Filler composition can be added to raise the site to the level of the surrounding area. The injection can be used superficially for wrinkle correction over the foramen and larger vessels.

In some embodiments involving the lower face, intradermal injections can be made using threading, bolus, and serial puncture at multi-directional grid deficits in perioral, chin, lower face. In some embodiments involving the upper face, intradermal injections can be made using threading, bolus, and serial puncture at multi-directional grid deficits in the periorbital, brow, zygoma, and upper face.

In some embodiments, the dynamic injection technique described herein addresses multi-direction indications. In some embodiments, to correct lateral lip atrophy and/or frown, a lateral lip border and an upper lip corner atrophy can be injected to lift the corner of the mouth. This can reduce oral commissure defects and marionette lines.

In some embodiments involving the correction of the jowl from chin atrophy, specific areas of muscle and/or fatty prominence visible in at least one expression are avoided. Filler composition can be injected into areas of specific deficit such that generalized atrophy reveals less shadowing during animation and at rest. By injecting these areas and restoring volume to the midline lower face, jowls are greatly reduced, and marionette lines and shadows are reduced by the fuller lower face.

In some embodiments, the filler composition can be injected into a mandibular area at a periosteum. In some embodiments, the injectable filler composition can be intradermally injected into a mandibular area. In some embodiments, the injection of the filler composition to the mandibular area is done in combination with an injection at any of the locations described herein. Additionally, the mandibular area can be injected both at the periosteum and intradermally to elevate and/or firm the soft tissues away from the bone. This can give the appearance of a face-lift, pulling out and down instead of up.

The amount of filler composition administered at each point can be in the range of from about 0.01 cc to about 1 cc, for example 0.01-0.05, 0.05-0.1, 0.1-0.15, 0.15-0.2, 0.2-0.3, 0.3-0.4, 0.4-0.5, 0.5-0.6, 0.6-0.7, 0.7-0.8, 0.8-0.9, or 0.9-1 cc. In some embodiments, about 0.10 cc of injectable filler composition can be administered into the face at an intersection identified using the grid. In some embodiments, between about 0.05 cc to about 1 cc of injectable filler composition can be administered at an intersection identified using the grid. In some embodiments, a total volume of less than about 3.0 cc is administered. In some embodiments, a total volume of about 1.0 cc to about 3.0 cc is administered. In some embodiments, a total volume of about 1.0 cc to about 4.0 cc is administered. In some embodiment, aspiration is performed just prior to injection to avoid injection into vessels and/or foramen.

After administration, the subject can be observed during animation to ensure all expressions are smooth and natural. The subject can animate the face to ensure injection is effective. In some embodiments, additional injections are made. Additional injections can be added to the jaw line to smooth the face at rest and in animation, adding volume to redrape the skin over lower face structures. These injections can be intradermal or at the periosteum as specific anatomy allows or limits. The injections can be deep injections. Deep injection reduces the burden of the skin to contain the implant and improves volume benefits of the implant. In some embodiments, administration of the filler composition can be followed by massage.

Figure 4:
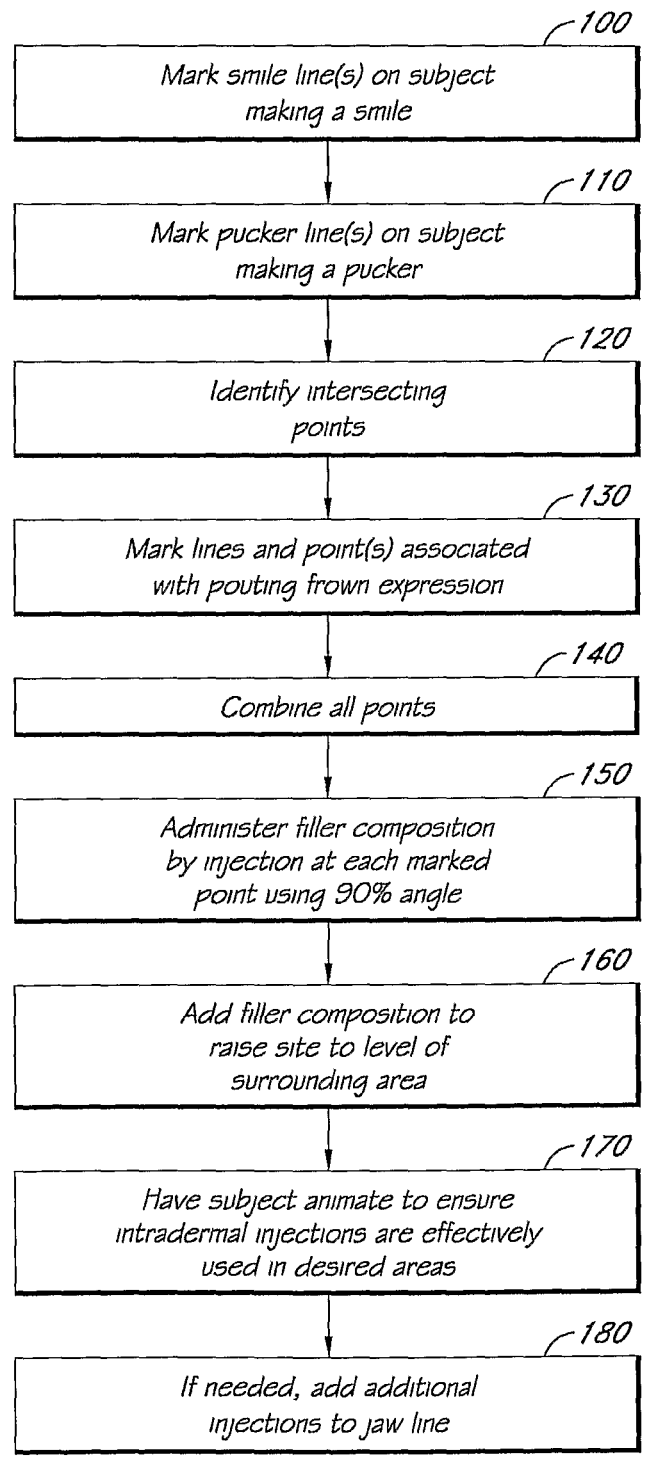
FIG. 4 depicts a flow chart detailing various possible steps that can be taken during some of the disclosed embodiments.

FIG. 4 is a flow chart depicting an additional specific embodiment of a system that can be used to perform a variety of methods or procedures. As shown at step 100, the smile line(s) on a subject making a smile are marked. The subject can make a pucker, and the pucker line(s) are marked 110. The intersection point(s) between the marked lines can be identified 120. The subject can make a pouting frown expression, and associated lines and point(s) are marked 130. The intersection point(s) identified in 120 can be combined 140 with the pouting frown expression depression lines and point(s) 130. Filler composition can be administered by injection at each marked point using a 90 degree angle 150. In some embodiments, the filler composition can be administered by injecting a bolus of the injectable filler composition after aspirating the syringe to verify that one has avoided the vessels and/or foramen. Filler composition can be added to raise the site to the level of the surrounding area 160. The injection can be used in areas requiring firming, or wrinkle correction over the foramen and larger vessels. The subject can animate the face to ensure injection is effective 170. Additional injections can be added to the jaw line to smooth the face at rest and in animation, adding volume to redrape the skin over lower face structures. These injections can be intradermal or at the periosteum as specific anatomy allows or limits. As with other embodiments described herein, those skilled in the art will appreciate that it is not necessary to mark each and every line and intersection, nor to make injections at each and every marked point.

As will be appreciated by one of skill in the art, there are a number of advantages that can result from using one, part, or some combination of the dynamic injections techniques described herein as compared to a traditional or "static" or single expression technique. As will be appreciated by one of skill in the art, not all, some, or any of the following listed advantages need to be present in any given embodiment. One of skill in the art, guided by the present disclosure, will be able to discern which embodiments will have which advantages.

As will be appreciated by one of skill in the art informed by the guidance provided herein, many traditional injection techniques only address one indication at a time. This can make unaddressed indications more conspicuous, compromising aesthetic outcome. As the dynamic technique can be applied generally over a larger area, the risk that this will happen can readily be reduced.

Additionally, because of differences between various embodiments of the dynamic techniques and the traditional techniques the expected or actual pain from practicing some of the current embodiments is much less than that from practicing a traditional technique. In some embodiments, the amount of pain from a dynamic injection procedure is less than 3 on a scale of 1-10 of pain perceived by a subject, where, typically, a similar resulting benefit from a traditional technique will vary as high as 10. Thus, in some embodiments, the dynamic injection procedure results in a third as much discomfort to the subject. One advantage of this is that less or no anesthesia need be used. Additionally, no nerve block need be used either. Thus in some embodiments, the dynamic injection technique is performed without nerve block. In some embodiments, the dynamic injection technique is performed without a topical anesthetic. As will be appreciated by one of skill in the art in light of the present disclosure, the absence of anesthesia (or stronger forms of anesthesia) can further provide for additional advantages for some of the embodiments. For example, the use of anesthesia can mask asymmetry, cause bruising, swelling, systemic issues, temporary paralysis, and asymmetry issues.

In some embodiments, use of the dynamic techniques described herein allows for aesthetically superior results. This can be observed in a number ways. In some embodiments, the desired results can be achieved more completely. In some embodiments, lines, voids, or wrinkles are visibly reduced to a greater extent than if traditional techniques had been used. In some embodiments, the facial features/expressions are supported at baseline to a greater extent. In some embodiments, multi-directional indications are resolved through using the present techniques. In some embodiments, the filler volume in the superficial tissues is more appropriate and natural looking. Additionally, because the filler placement is specific to the subject's anatomy and animation, the outcome will appear more customized for a more aesthetic outcome. In some embodiments, the subject's face is more aesthetically pleasing, even when animated.

In some embodiments, the use of the dynamic technique described herein allows for less dermal filler to be used in a subject. This can reduce the amount of time required for the application, reduce the cost of the application (as less filler is used), and reduce the recovery time required by the subject. In some embodiments, the dynamic technique uses less filler than the amount required by a traditional static technique of simply "filling the line" with filler. The amount of filler can be less than 100% of the amount used in a traditional technique, for example 100-90, 90-80, 80-70, 70-60, 60-50, 50-40, 40-30, 30-20, 20-10, and 10-5% as much filler as would have been used for addressing the same locations.

In some embodiments, the dynamic technique can take less time to perform than traditional techniques. As will be appreciated by one of skill in the art, a traditional technique to address the oral commissure can take 40-60 minutes, require 1-3 mL of filler, and vary in pain level from 1 to 10. A traditional technique to address the marionette lines/jowl can take 30-60 minutes, 1-4 ml of filler and vary in pain level from 1 to 10. A traditional technique to address the lips/frown can take 40-60 minutes, 1-2 ml of filler and vary in pain level from 1 to 10. A traditional technique to address the tear trough/brow lift can take 40-60 minutes, 1-2 ml of filler and vary in pain level from 1 to 10. In contrast, some embodiments of the dynamic technique can address these issues in less time, with less pain and less filler. For example, some embodiments of the dynamic technique to address the lower face employ 1-3 ml of filler, take 30-40 minutes and vary in pain from 1-3 (on a pain scale of 1-10 with 10 being the highest). In some embodiments, the dynamic technique to address the upper face employs 1-3 ml of filler, take 30-40 minutes and vary in pain from 1-3. In some embodiments, the dynamic technique to address the upper face employs 1-4 ml of filler, take 30-40 minutes and vary in pain from 1-3. It is noted that, generally speaking, by using various embodiments of the dynamic technique, one can address about half of the face in less time, with less pain, and with a comparable amount of filler as a traditional technique employs for a single issue in the face.

In some embodiments, the methods and systems disclosed herein allow for improved administration of injectable filler compositions. More particularly, some embodiments disclosed herein provide for targeted, subject anatomy-specific administration of filler compositions. Thus, in some of the embodiments, the methods and systems disclosed herein provide increased aesthetic benefit by customizing for a "natural" aesthetic outcome. Some of the embodiments disclosed herein provide methods and systems that address difficult to correct indications quickly, use reduced amounts anesthetic, have reduced amounts of downtime, and take less injection time than conventional methods.

Some of the indications which can be addressed by the systems and methods disclosed herein include: oral commissure, marionette lines, mandibular hollow, raise jowl, frowning mouth, pout lower lip, later expression lines, mental crease, chin dimpling, zygomatic hollow, nasolabial furrow, tear trough, and brow lift. In some embodiments, the administration of filler composition enables redraping of the skin by smoothing the spaces between the muscle groups and bone that either were, or never were, aesthetically approximated for smooth animation. In some embodiments, the administration of filler composition ensures that the animating face, as well as the resting face, is corrected according to the movement pattern of the individual subject. Injections can be placed according to the deficits identified in a grid identified from the subject's own animations.

The injection technique for traditional techniques can be intradermal. Intradermal injections are typically made with insertion at a 10 to 20 degree angle, then proceeding forward at a zero degree angle once at proper depth.

As will be appreciated by one of skill in the art, in light of the present disclosure, there are a number of issues or effects that are common in prior injection techniques. Various embodiments described herein can address some or all of these issues. For example, traditional techniques may only address intradermal indications and use more product less accurately. Additionally, product volume in superficial tissues may be over filled to get a correction, which may not be aesthetically pleasing. Previous techniques had a tendency to result in patient expressions looking "unfamiliar" to patient. Additionally, as the filler placement was not specific to patient musculature/movement it ran the risk of looking less "natural." Similarly, previous filler placement would reveal deficits or hollows caused by muscle movement after treatment. Lips could look unnaturally large "fish lips." Frequently, facial features or expressions were not supported following injections. Additionally, soft tissue may not have been leveraged strategically, elevating skin outward away from bone using bidirectional deficits. Additionally, direct, traditional, placement of a dermal filler can cause redundant fullness and drooping appearance of eyelid/brow, bulging of tear trough, eye "puffiness." In some embodiments, at least one of the above is reduced or eliminated through the use of the dynamic technique instead of a traditional technique. The above issues can be especially noticeable when dealing with one of the following locations: oral commissure, corner of mouth raised, lips, marionette lines, nasolabial furrow, and tear trough, brow. As will be appreciated by one of skill in the art, not all of the disclosed embodiments need address any, some, or all of the above noted issues.

In some embodiments, methods and systems disclosed herein provide for ease of training or instruction for the administration of an injectable filler composition to a subject. As is appreciated by one of skill in the art, in some situations, because of variations in individual anatomy and structure, it can be difficult to obtain reproducible results using conventional administration methods. Additionally, as will be appreciated by one of skill in the art, to some extent, the application of dermal fillers in the cosmetics industry can be characterized as more of an "art" than a science. In other words, training people in this process can often be a trial and error experience rather than involving a clear set of instructions and signposts to follow. These issues can be problematic when attempting to instruct others on how to administer an injectable filler composition. In some of the embodiments disclosed herein, this and other considerations have resulted in various training methods that can address some or all of these issues.

Thus, in some embodiments, provided herein are systems and methods that can be, relatively speaking, readily and/or clearly taught. In some embodiments, this involves teaching others how to use the dynamic injection (e.g., dynamic grid) system described herein. In some embodiments, the dynamic grid technique lends itself to ready communication to others and discussion of how and why the technique works. Additionally, in some embodiments, the technique can be readily applied by numerous and different people with different backgrounds. That is, in some embodiments, the teaching of the above dynamic grid system provides for increased reproducibility of the results described herein with the relevant products. In some of the embodiments, providing users with the knowledge of these methods provides quality control for the administration of a filler composition. Thus, in some embodiments, a method for teaching a technique that is especially amenable to teaching (and/or the other aspects noted above) is provided. In some embodiments, the teaching of the method itself also provides the above noted advantages of providing users with a basic technique in common, reproducibility and predictability of results, and allowing a broader range of people to apply the filler. Of course, the application of the technique itself can have the specific advantages noted herein as well.

Figure 5:
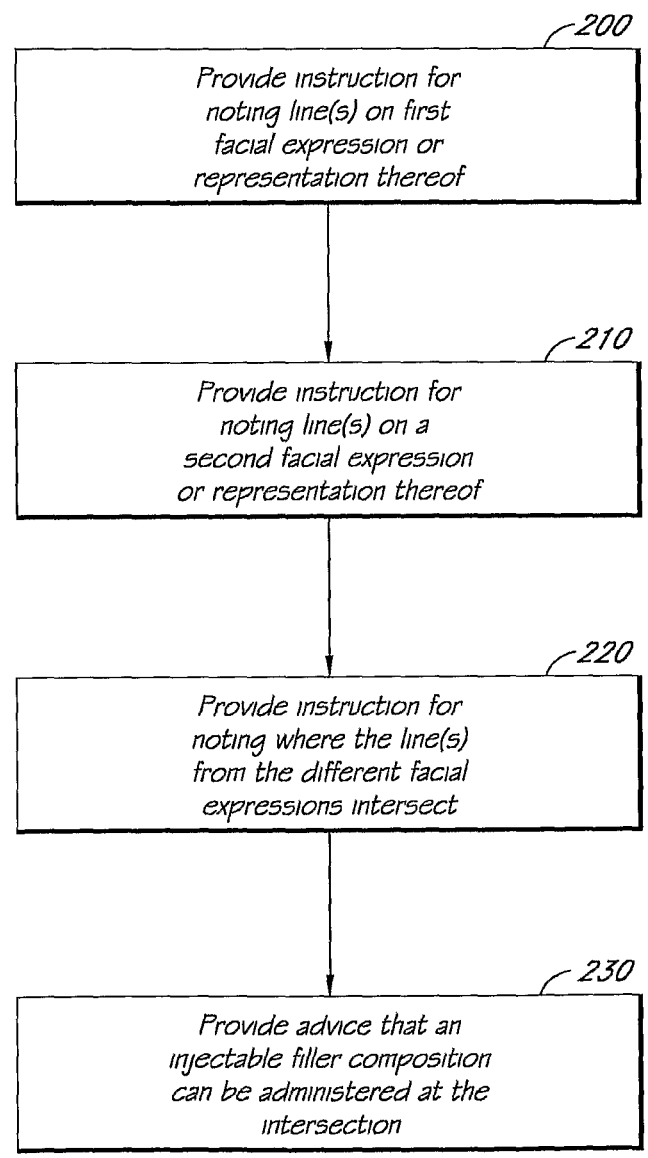
FIG. 5 depicts a flow chart describing various possible steps that can be taken during some of the disclosed training embodiments.

FIG. 5 depicts a flow chart depicting an embodiment of a system that can be used to teach or train a user to perform one embodiment of the dynamic grid technique. As shown at step 200, instructions are provided to the user that the user should note a line(s) on a first facial expression or representation thereof 200. Suitable facial expressions are described in detail above. Instructions are also provided to the user that they should note a line(s) on a second facial expression or representation thereof, in step 210. In some embodiments, instructions are also provided to a user that they can note a line(s) on any number of subsequent facial expressions or representations thereof. Instructions are also provided to the user that they identify where the line(s) identified from the different facial expressions intersect with one another, in step 220. Instructions are also provided to the user that they inject the filler composition at or to the intersect, in step 230.

Representations of a facial expression can be provided using a wide variety of media. In some embodiments, the representation of a facial expression is a diagram, a drawing, a photograph, a cartoon, a sketch, a video, a statue, a live demo on a mannequin, model, living face, or a mold.

Instructions can be provided using a wide variety of media. In some embodiments, the instructions can be provided orally, in printed material, or in digital format. The instructions can be provided in a video, on a CD-ROM, in an instruction booklet, in a book, in a DVD, or in MP3 format, Webinar, Webcast with or without visuals, etc. The instructions can be presented in a classroom, a hospital or in an office.

As will be appreciated by one of skill in the art, the training method described herein provides for more than simply allowing others in the field to use the technique. As noted above, it establishes a common framework within which those in the field can more readily operate. Additionally, the above training technique can help to standardize the technique and results. Additionally, the fact that the technique lends itself to training, because of the relatively clear steps and relatively clear signposts to be followed, further emphasize the usefulness of this training technique. In some embodiments, the people that are trained will then go out and perform the technique.

As will be appreciated by one of skill in the art, various training aids can be used in the training method, including those aspects discussed below in the kit. For example, in some embodiments, one step in the training method is to display the results of the dynamic method, or to discuss any of the advantages of the dynamic technique over a traditional technique. In some embodiments, any of the steps, properties, advantages, or embodiments of the various dynamic techniques discussed herein can be employed as part of the training technique.

In some embodiments, a training kit is provided. The kit can include instructions or guidance for performing parts of or all of some or all of the above techniques. The instructions can be provided on a variety of formats, such as electronic (data file, DVD, downloadable, etc) or pamphlets. The instructions can generally provide one with any of the steps outlined herein. For example, the instructions can include information regarding how much to inject, the amount of time it may take for a procedure and for patient recovery after the procedure, the amount of pain that occurs during the procedure, the relative amount of pain of a dynamic procedure compared to various traditional procedures, advantages of the dynamic technique over static techniques, the results that can be expected, how the injections should be made in particular situations, and identify additional injection sites that could generally be beneficial for certain aspects, even if they are not identified via the dynamic technique. In some embodiments, the training kit includes before and after depictions of subjects that have received the treatment.

In some embodiments, the kit includes a marking device, such as a pen, to mark the first and second set of lines for the grid or for identifying the areas that may not have as much volume as desired. In some embodiments, at least two different colored marking devices are included, to readily allow one to identify which lines belong to which facial expression.

In some embodiments, the kit includes a sample of a dermal filler. In some embodiments, the dermal filler is RESTYLANE™ or PERLANE® dermal filler.

In some embodiments, the kit also includes a syringe. The syringe can be a 2 ml or smaller syringe. In some embodiments, the syringe is prefilled with the dermal filler.

In some embodiments, the kit includes gloves. In some embodiments, the kit includes sterilizing material. In some embodiments the kit includes a cloth or other absorbent material.

In some embodiments, the kit includes software for assisting in capture images of the subject's face and/or identifying areas that lack volume, wrinkles, lines, etc. in various facial expressions. In some embodiments, the software compares two facial expressions of the subject and determines where one should inject the dermal filler by identifying the sections in the first and second facial expressions that overlap.

As will be appreciated by one of skill in the art, in some embodiments, the training kit not only provides training for the user of the technique, but can also provide additional information to help the user sell the technique to potential clients. In some embodiments, the kit includes information to help the user order additional dermal filler.

As will be appreciated by one of skill in the art, in some embodiments, the above techniques and methods need not be applied only in connection with the use of an injectable filler. In some embodiments, any method or technique that thickens, or improves the rigidity of the subject's skin can be used together with the presently disclosed techniques. For example, the lack of volume analysis or grid based technique can be used with non-injection techniques, e.g., the application of light energy or radio-frequency energy to the subject's skin (e.g., such as in THERMAGE® a radiofrequency based technology employing monopolar capacitive RF technology or ELOS™ energy based technology). In some embodiments, anything that stimulates collagen growth can be applied in conjunction with the above methods. In some embodiments, the technique improves the appearance of the thickness of the skin, rigidity of the skin, the appearance of volume of the skin, and/or increases the appearance of firmness of the skin. As will be appreciated by one of skill in the art, an improvement in the appearance of thickness, rigidity, volume, and/or firmness can be observed directly, and/or via the removal of lines and/or wrinkles.

EXAMPLES

Example 1

Grid Application

This example generally outlines how one can apply an injectable filler composition using one embodiment of the dynamic grid. The subject will flex a first muscle group that pulls a section of skin in a first manner. Wrinkles and lines that are visible in the section of skin in the first flexed position will be identified. This can be achieved by tracing the wrinkle or line on the subject's skin with a marker. The subject will then flex a second muscle group. This second muscle group will pull the section of skin in an opposing direction to that pulled by the first muscle group. The wrinkles and/or lines that are visible in the second flexed position will be identified via tracing the wrinkle or line on the subject's skin with a marker. A dermal filler will then be injected into the subject according to where the first markings and second markings intersect. As sufficient amount of dermal filler will be injected so that the first, second, or both lines or wrinkles are visibly reduced.

The result will be that the visible wrinkles and lines in the subject will be reduced. The filler can be RESTYLANE™ or PERLANE® dermal filler. In some situations, a topical anesthetic or a cooling agent can be used prior to or with the application of the dermal filler.

Example 2

Grid Application, Lower Face

This example describes how one can apply an injectable filler composition to the lower face of a subject using a dynamic grid technique. The subject will sit up during the injection. The subject will make a first facial expression. The lines/wrinkles, etc. that are observable in the first facial expression in the lower face will be marked on the subject's lower face using washable ink. The subject will then make a second facial expression and the lines/wrinkles, etc. that are observable in the second facial expression will also be marked on the subject's lower face. The facial expressions can include a smile, lip pucker, frown, etc. The markings from the first and second facial expressions will intersect at, at least one intersection point. One will then inject a dermal filler by placing boluses of the filler according to the line intersects. These injections can be supra-periosteal (inserting the needle at a 90 degree angle to face).

One can then inject using threading, bolus, and/or serial puncture at areas not directly addressed by the grid, such as in perioral, chin, and the lower face. These injections can be intradermal.

One can then observe the subject's face during animation to ensure that all expressions are smooth and natural. If any locations require additional adjustments, adjustments can be made by adding intradermal and/or deep injections and/or massage.

The result will be that the wrinkles/lines, etc., will be visibly reduced. Additionally, for the resulting benefit, the subject will experience relatively less discomfort or pain than if a traditional, static technique had been used. The injection process can take 30 to 40 minutes and 1-3 mL of filler can be used. The filler can be RESTYLANE™ or PERLANE® dermal filler.

In some situations, a topical anesthetic or a cooling agent can be used prior to or with the application of the filler.

The indications addressed by this process can include the following: oral commissure, marionette lines, mandibular hollow, raise jowl, frowning mouth, pout lower lip, lateral expression lines, mental crease, and chin dimpling.

Example 3

Grid Application, Upper Face

This example describes how one can apply an injectable filler composition to the upper face of a patient using a dynamic grid technique. The subject will sit up during the injection. The subject will make a first facial expression. The lines/wrinkles, etc. that are observable in the first facial expression will be marked on the subject's upper face via washable ink. The subject will then make a second facial expression and the lines/wrinkles, etc. that are observable in the second facial expression will also be marked on the subject's upper face. The facial animations can include a smile, lip pucker, frown, etc. One will then inject an injectable filler composition by placing boluses of the filler according to the markings created during the two facial expressions intersect. These injections can be supra-periosteal (inserting the needle at a 90 degree angle to face).

One can then inject using threading, bolus, and/or serial puncture at areas not directly addressed by the grid, such as in periorbital, brow, zygoma, and/or upper face. These injections can be intradermal.

One can then observe the subject's face during animation to ensure that all expressions are smooth and natural. If any locations require additional adjustments, they can be made by adding intradermal and/or deep injections and/or massage.

The result will be that the wrinkles/lines, etc., will be visibly reduced. Additionally, for the resulting benefit, the subject will experience relatively less discomfort or pain than if a traditional, static technique had been used. The injection process can take 30 to 40 minutes and 1-3 mL of filler can be used. The filler can be RESTYLANE™ or PERLANE® dermal filler.

In some situations, a topical anesthetic or a cooling agent can be used prior to or with the application of the filler.

The indications/results addressed by this technique can include the following: zygomatic hollow, nasolabial furrow, tear trough, and brow lift.

Example 4

Grid Application, Neck

The subject will flex a first muscle group that pulls a section of skin in the subject's neck in a first manner. Wrinkles and lines that are visible in the first flexed position will be marked on the subject's neck. The subject will then flex a second muscle group that pulls on the section of skin in the subject's neck in a second manner. This can be a muscle group that pulls the skin in an opposing direction to the direction of the first muscle group. The wrinkles and lines that are visible in the second flexed position will be marked. An injectable filler composition will be injected into the subject according to where the first markings and second markings intersect.

The result will be that the visible wrinkles and lines in the subject will be reduced. The filler can be RESTYLANE™ or PERLANE® dermal filler. In some situations, a topical anesthetic or a cooling agent can be used prior to or with the application of the filler.

Example 5

Grid Application, Body

The subject will flex a first muscle group in the subject's leg. Wrinkles and lines that are visible in the first flexed position will be marked or identified on the subject's leg. The subject will then flex a second muscle group in the subject's leg, preferably a muscle group that pulls the tissue to be addressed in the opposite direction that the first muscle group pulled the skin. The wrinkles and lines that are visible in the second flexed position will be marked or identified. An injectable filler composition will be injected into the subject according to where the first markings and second markings intersect.

The result will be that the visible wrinkles and lines in the subject will be reduced. The filler can be RESTYLANE™ or PERLANE® dermal filler. In some situations, a topical anesthetic or a cooling agent can be used prior to or with the application of the filler.

Example 6

Animated Volume Defficient Injection, Lower Face

This example describes how one can apply a dermal filler using a dynamic injection technique. The subject will make a first facial expression. Areas or locations of the subjects face that appear to lack volume will be identified. The subject will then make a second facial expression and areas or locations of the subject's face that appear to lack volume in the second facial expression will be identified. The facial animations can include a smile, lip pucker, frown, etc. One will then inject a dermal filler by placing boluses of the filler in areas that appear to lack volume in both the first and second facial expression. That is, the injections will be administered at locations where the areas or locations lacking volume between the two facial expressions overlap. These injections can be supra-periosteal (inserting the needle at a 90 degree angle to face).

One can then inject using threading, bolus, and/or serial puncture at additional areas, such as in perioral, chin, and the lower face. These injections can be intradermal.

One can then observe the subject's face during animation to ensure that all expressions are smooth and natural. If any locations require additional adjustments, they can be made by adding intradermal and/or deep injections and/or massage.

The result will be that the wrinkles/lines, etc., will be visibly reduced. Additionally, for the resulting benefit, the subject will experience relatively less discomfort or pain than if a traditional, static technique had been used. The injection process can take 30 to 40 minutes and 1-3 mL of filler can be used. The filler can be RESTYLANE™ or PERLANE® dermal filler.

In some situations, a topical anesthetic or a cooling agent can be used prior to or with the application of the filler.

The indications addressed by this process can include the following: oral commissure, marionette lines, mandibular hollow, raise jowl, frowning mouth, pout lower lip, lateral expression lines, mental crease, and chin dimpling.

Example 7

Animated Volume Defficient Injection, Upper Face

This example describes how one can apply a dermal filler using a dynamic technique. The subject will sit up during the injection. The subject will make a first facial expression. Areas of the subject's face that appear to lack volume will be identified. The subject will then make a second facial expression and areas of the subject's face that appear to lack volume in the second facial expression will be identified. The facial animations can include a smile, lip pucker, frown, etc. One will then inject a dermal filler by placing boluses of the filler in areas that appear to lack volume in both the first and second facial expression. That is, the injections will be administered at locations where the areas or locations lacking volume between the two facial expressions overlap. These injections can be supra-periosteal (inserting the needle at a 90 degree angle to face).

One can then inject using threading, bolus, and/or serial puncture at areas such as in periorbital, brow, zygoma, and/or upper face. These injections can be intradermal.

One can then observe the subject's face during animation to ensure that all expressions are smooth and natural. If any locations require additional adjustments, they can be made by adding intradermal and/or deep injections and/or massage.

The result will be that the wrinkles/lines, etc., will be visibly reduced. Additionally, for the resulting benefit, the subject will experience relatively less discomfort or pain than if a traditional, static technique had been used. The injection process can take 30 to 40 minutes and 1-3 mL of filler can be used. The filler can be RESTYLANE™ or PERLANE® dermal filler.

In some situations, a topical anesthetic or a cooling agent can be used prior to or with the application of the filler. The indications/results addressed by this technique can include the following: zygomatic hollow, nasolabial furrow, tear trough, and brow lift. In some situations, the injection of the filler is at and/or within the subcutis, superficial subcutis, and/or the deep dermis.

Example 8

Instructing Dynamic Techniques

This example demonstrates how one can train someone regarding a dynamic injection technique.

The trainee (or user) is directed to identify a first area in a subject that appears to lack a desired amount of volume under the skin. The trainee is directed to wait for the subject to, or request that the subject make, a different facial expression. The trainee is directed to identify a second area in the subject that appears to lack a desired amount of volume under the skin. The trainee is instructed that, where the two areas overlap is an indication of where a dermal filler should be added.

The directions can be provided in person, by voice alone, in a conference format, by video, in an electronic format, in printed material, etc.

Example 9

Instructing Grid Techniques

This example demonstrates how one can train someone regarding a dynamic grid injection technique.

The trainee is directed to identify and trace a first set of wrinkles/lines in a subject that is making a first facial expression. The trainee is directed to wait for the subject to, or request that the subject make, a different facial expression. The trainee is directed to identify and trace a second set of wrinkles/lines one the subject. The trainee is instructed that the location of injection of the dermal filler is where a line from the first set of lines intersects with a line from the second set of lines.

The directions can be provided in person, by voice alone, in a conference format, by video, in an electronic format, in printed material, etc.

Example 10

Providing Instructions for Dynamic Technique

This example demonstrates one way of providing training instructions for those that may wish to employ a dynamic injection technique.

At least one person that is interested in learning at least one aspect of the dynamic injection technique is present in a room with at least one spokesperson that will provide general guidance regarding the dynamic technique. The spokesperson will note that using a dynamic technique to identify locations to apply a dermal filler is one way of applying a dermal filler to a subject. The spokesperson can note that one can look for areas that are lacking in volume between different facial expressions and that one should apply the dermal filler to those locations. Alternatively, or in addition, the spokesperson can note that one can employ the dynamic grid to identify appropriate locations for injection.

By performing the above, instructions will be provided regarding the dynamic injection technique.

Example 11

Providing Instructions for Dynamic Technique

This example demonstrates one way of providing training instructions for those that may wish to employ a dynamic injection technique.

At least one person that is interested in learning at least one aspect of the dynamic injection technique is provided with a downloadable audio or video file that will provide general guidance regarding the dynamic technique. The file will include content that will specify that using a dynamic injection technique to identify locations to apply a dermal filler is one way of applying a dermal filler to a subject. The content will specify that one look for areas that are lacking in volume between different facial expressions, and that one apply the dermal filler to those locations. Alternatively, or in addition, the content can note that one can employ the dynamic grid to identify appropriate locations for injection.

By performing the above, instructions will be provided regarding the dynamic injection technique.

Example 12

Providing Instructions for Dynamic Technique

This example demonstrates one way of providing training instructions for those that may wish to employ a dynamic injection technique.

A pamphlet is provided to at least one person that is interested in learning at least one aspect of the dynamic technique. The pamphlet will provide general guidance regarding the dynamic technique. The pamphlet will include content that will specify that using a dynamic technique to identify locations to apply a dermal filler is one way of applying a dermal filler to a subject. The pamphlet can specify that one can look for areas that are lacking in volume between different facial expressions, and that one should apply the dermal filler to those locations. Alternatively, or in addition, the pamphlet can note that one can employ the dynamic grid to identify appropriate locations for injection.

By performing the above, instructions will be provided regarding the dynamic injection technique.

Example 13

Providing Instructions for Dynamic Technique

This example demonstrates one way of providing training instructions for those that may wish to employ the various dynamic injection techniques.

A DVD is provided to at least one person that is interested in learning at least one aspect of the dynamic injection technique. The DVD will provide general guidance regarding the dynamic technique. The DVD will include content that will specify that using a dynamic technique to identify locations to apply a dermal filler is one way of applying a dermal filler to a subject. The content will specify that one look for areas that are lacking in volume between different facial expressions, and that one apply the dermal filler to those locations. Alternatively, or in addition, the content can note that one can employ the dynamic grid to identify appropriate locations for injection.

By performing the above, instructions will be provided regarding the dynamic injection technique.

Example 14

Providing Instructions for Dynamic Technique

This example demonstrates one way of providing training instructions for those that may wish to employ the various dynamic injection techniques.

Some or all of the aspects of at least one of the above examples (10-13) can be carried out in conjunction with some or all of the aspects of at least one of the other above examples (10-13) so that various pieces of information are provided in various manners. This can provide for a more effective way of providing instructions regarding the dynamic technique.

In some situations, the general background information regarding the dynamic injection technique is provided by a spokesperson, while the instructions regarding the technique itself are provided in an audio/video format.

By performing the above, instructions will be provided regarding the dynamic injection technique.

Example 15

Non-Injection Based Applications

This example demonstrates how one can apply a non-injection based technique in accordance with some of the present embodiments. As will be appreciated by one of skill in the art, this example can be applied to any technique or process that provides for an increase in volume and/or firmness in the subject's skin.

First, one identifies an area of treatment, this can be done as generally outlined in the above examples. For example, the subject will make a first facial expression. Areas of the subject's face that appear to lack volume will be identified. The subject will then make a second facial expression and areas of the subject's face that appear to lack volume in the second facial expression will be identified. The facial animations can include a smile, lip pucker, frown, etc. Areas identified during the first and second facial expressions that overlap will be characterized as areas that are under volume. In some embodiments, the grid based approach is used to identify the areas to be treated.

Once the area to be treated is identified, a method or technique that thickens, improves the rigidity of the subject's skin, and/or stimulates collagen growth will be applied to that area. This technique can include or be light energy and/or radio-frequency energy that is applied to the subject's skin (e.g., such as in THERMAGE® based technology employing monopolar capacitive RF technology or ELOS™ (Electro-optical synergy) technology). In some embodiments, the light energy and/or radio-frequency energy is applied in a relatively focused manner to those areas that have been identified above. In some embodiments, the light energy or radio-frequency energy is applied only to those areas identified above.

In some embodiments various forms of treatment (e.g., injection based, light based, RF based, and/or heat based) are applied to the subject at the identified location and/or at various locations on the subject's face or area to be treated. In some embodiments, all of the light and/or RF energy is focused onto the area to be treated. However, as will be appreciated by one of skill in the art, not all of the light need be focused onto the treatment area (for example less than 100, 100-95, 95-90, 90-80, 80-70, 70-60, 60-50, 50-40, 40-30, 30-20, 20-10, or less than 10% of the emitted light can be directed to the identified location).

Example 16

Identification of Under Volume Areas

This example demonstrates how one can use some embodiments to identify where a subject lacks sufficient volume under or in their skin.

The subject will make a first facial expression. A first area of the subject's face that appears to lack volume during the first facial expression will be identified. The subject will then make a second facial expression and a second area of the subject's face that appears to lack volume in the second facial expression will be identified. The facial animations can include a smile, lip pucker, frown, etc. Areas that overlap between the first and second areas identified during the first and second facial expressions will be locations that are under volume or generally locations of interest.

In some situations, the first or second facial expression is an expression at rest. In some embodiments, the first or second area(s) that appear(s) to lack volume will be an area of, or exacerbated by, injury or scarring. Thus, in some embodiments, a scar or other imperfection can be used in a similar manner as a wrinkle, line, or area having an insufficient volume. In some situations, the first and second areas are not areas of, or exacerbated by injury or scarring. Thus, in some embodiments, areas of injury or scarring are excluded as areas that have an insufficient volume or that include a line or wrinkle. In some embodiments, the present techniques are not applied to scarred or injured areas.

Example 17

Identification of Under Volume Areas, Grid

This example demonstrates how one can use some embodiments to identify where problem areas exist (such as areas that are under volume) in a subject.

The subject will make a first facial expression. A first wrinkle and/or line on the subject's face that is present during the first facial expression will be identified (and optionally traced or marked). The subject will then make a second facial expression and a second wrinkle and/or line on the subject's face that is present during the second facial expression will be identified (and optionally traced or marked). The facial animations/expressions can include a smile, lip pucker, frown, etc. Wrinkles and/or lines that overlap between the first and second facial expressions will indicate locations of interest (at the area of the intersection of the first and second lines or wrinkles).

Example 18

Method of Directing One to Locate Under Volume Areas

This example demonstrates how one can use some embodiments to direct people how to locate problem areas (such as areas that are under volume) in a subject.

At least one person that is interested in learning at least one aspect of the dynamic injection technique is present in a room with at least one spokesperson. The spokesperson will display a first representation of a wrinkle in a subject when a first muscle (or set of muscles) is contracted. The spokesperson will display a second representation of the area in the subject when a second muscle (or set of muscles) is contracted. The area will indicate at least a second wrinkle. The spokesperson will note that the location of the wrinkles in the first and second representations will be noted. The spokesperson will note that points of intersection between the wrinkles from the first set and the wrinkles from the second set will represent areas that are under volume.

In some embodiments, an injection aid is provided. The injection aid includes a series of depictions in which 1) at least a first wrinkle is depicted along with a marking line tracing at least a part of the wrinkle (wherein a first muscle is contracted to provide the first wrinkle), 2) a second wrinkle is depicted along with a marking line tracing at least a part of the second wrinkle (wherein a second muscle is contracted to provide the second wrinkle), and 3) the intersection point(s) between the first and second of lines. In some embodiments, items 1 and 2 are depicted on separate pages or parts of the aid. In some embodiments, the markings are depicted in separate colors or by distinguishable characteristics. In some embodiments, the pages are transparent, allowing for markings from the first set of wrinkles to be depicted over or with the markings from the second set of wrinkles.

In this disclosure, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. The phrase "and/or" denotes a shorthand way of indicating that the specific combination is contemplated in combination and, separately, in the alternative.

The section headings used herein are for organizational purposes only and are not to be construed as limiting the described subject matter in any way.

It will be appreciated that there is an implied "about" prior to the amounts, concentrations, times, etc. discussed in the present teachings, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the invention.

The various devices and systems described above provide a number of ways to carry out the invention. It is to be understood that not necessarily all objectives or advantages described can be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls.

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A method for identifying and marking an area that lacks volume in a subject, said method comprising the steps of:
    identifying and marking on said subject at least a first area lacking volume, the first area comprising a first wrinkle that is present when a first muscle is contracted; and
    identifying and marking a second area comprising a second wrinkle that is present when a second muscle is contracted, wherein said first area and said second area overlap at the area that lacks volume.

2. The method of claim 1, further comprising the step of:
    injecting an injectable filler composition at said area that lacks volume.

3. The method of claim 2, wherein the injecting step comprises:
    injecting said injectable filler composition at a first location in said area that lacks volume, the intersection location being located along a muscle selected from the group consisting of M. caninus, M. orbicularis oris, M. mentalis, M. indisivus labii inferioris, M. triangularis, M. buccinators, and M. masseter.

4. The method of claim 2, wherein the injecting step comprises:
    injecting said injectable filler composition at a first location in the area that lacks volume, the first location being located along a feature selected from the group consisting of a jowl, a marionette line, a mental crease, an oral commissure and a levator obicularis fold.

5. A method for administering an injectable filler composition to a subject, said method comprising:
    identifying at least a first facial line on a subject having a first facial expression;

identifying at least a second facial line on said subject having a second facial expression, wherein said second facial line has at least one intersection location with said first facial line; and injecting the injectable filler composition into said face of said subject at said at least one intersection location.

6. The method of claim 5, wherein said step of injecting filler comprises:

injecting said injectable filler composition at a tissue selected from the periosteum, the subcutis, the intradermal plane, and any combination thereof, by administration within limits of said tissue to hold the injectable filler.

7. The method of claim 5, wherein the injecting step comprises:

injecting said injectable filler composition at the intersection location, the intersection location being located along a muscle selected from the group consisting of *M. caninus, M. orbicularis oris, M. mentalis, M. indisivus labii inferioris, M. triangularis, M. buccinators*, and *M. masseter.*

8. The method of claim 5, wherein the injecting step comprises:

injecting said injectable filler composition at the intersection location, the intersection location being located along a feature selected from the group consisting of a jowl, a marionette line, a mental crease, an oral commissure and a *levator obicularis* fold.

* * * * *